US010315001B2

(12) United States Patent
Lun et al.

(10) Patent No.: US 10,315,001 B2
(45) Date of Patent: Jun. 11, 2019

(54) CRANIUM CUDDLER

(71) Applicant: Valley Children's Healthcare, Madera, CA (US)

(72) Inventors: Michael Cam Lun, Modesto, CA (US); Daniel Oh, Carson, CA (US); Kiran Chauhan, Fresno, CA (US); Ashley Hall, Manteca, CA (US); Andrew Yfantis, Saratoga, CA (US); Nadarasa Visveshwara, Fresno, CA (US)

(73) Assignee: VALLEY CHILDREN'S HEALTHCARE, Madera, CA (US)

( * ) Notice: Subject to any disclaimer, the term of this patent is extended or adjusted under 35 U.S.C. 154(b) by 12 days.

(21) Appl. No.: 15/430,286

(22) Filed: Feb. 10, 2017

(65) Prior Publication Data

US 2017/0151408 A1   Jun. 1, 2017

Related U.S. Application Data

(63) Continuation of application No. PCT/US2016/020735, filed on Mar. 3, 2016.
(Continued)

(51) Int. Cl.
*A61M 16/06* (2006.01)
*A61F 9/04* (2006.01)
*A61M 16/08* (2006.01)

(52) U.S. Cl.
CPC .......... *A61M 16/0683* (2013.01); *A61F 9/04* (2013.01); *A61M 16/0666* (2013.01);
(Continued)

(58) Field of Classification Search
CPC .......... A61M 16/00; A61M 16/0003–16/0012; A61M 16/06–16/0694;
(Continued)

(56) References Cited

U.S. PATENT DOCUMENTS 3,161,199 A * 12/1964 Sands ................ A61M 25/02
                                                       128/207.18
3,171,133 A    3/1965 Steffen
(Continued)

FOREIGN PATENT DOCUMENTS

WO    2009/149375    12/2009

*Primary Examiner* — Tan-Uyen T Ho
*Assistant Examiner* — Ned T Heffner
(74) *Attorney, Agent, or Firm* — Peacock Law P.C.; Janeen Vilven

(57) ABSTRACT

A headgear for securing a patient airway interface device to a patient's head comprising a concave partial helmet having an outer surface and an inner surface and having a left lateral element, a right lateral element, a top portion and a back portion, wherein the left lateral element and the right lateral element are separated at a front half of the concave partial helmet by a void between the front half top portion of the concave partial helmet and the left lateral element and the right lateral element; when on the patient's head the top portion of the concave partial helmet terminates at the forehead of the patient's head with a front face of the top portion of the concave partial helmet that is proximal to the forehead having a stabilizer for supporting a hub and wherein the left lateral element and the right lateral element is structured to terminate on either side of a patient's face near a cheek portion without directly touching the check portion and wherein a section of the right lateral element and the left lateral element that is near the cheek portion includes an opening that permits passage of a strap from the outer surface to the inner surface and wherein a portion of the inner surface of the concave partial helmet that is structured to overlay the back half of the skull when the headgear is in use is separated from the patient's head by a pliable material that is attached to the inner surface.

19 Claims, 24 Drawing Sheets

Related U.S. Application Data

(60) Provisional application No. 62/127,628, filed on Mar. 3, 2015.

(52) U.S. Cl.
CPC . *A61M 16/0875* (2013.01); *A61M 2205/3375* (2013.01); *A61M 2240/00* (2013.01)

(58) Field of Classification Search
CPC ...... A61M 16/20–16/209; B63C 11/12; B63C 11/18; A62B 18/00; A62B 18/10; A62B 7/00; A62B 7/04; A62B 7/14; A62B 9/02
See application file for complete search history.

(56) References Cited

U.S. PATENT DOCUMENTS

| | | | |
|---|---|---|---|
| 3,599,635 A | 8/1971 | Ansite | |
| 3,827,433 A | 8/1974 | Shannon | |
| 4,018,221 A | 4/1977 | Rennie | |
| 5,191,882 A | 3/1993 | Vogliano | |
| 5,577,495 A | 11/1996 | Murphy | |
| 5,662,101 A * | 9/1997 | Ogden | A61M 16/06 128/202.27 |
| 5,758,639 A | 6/1998 | Ikonen | |
| 6,385,780 B1 | 5/2002 | Racine | |
| 6,470,886 B1 | 10/2002 | Jestrabek-Hart | |
| 7,156,096 B2 | 1/2007 | Landis | |
| 7,455,063 B2 | 11/2008 | Geiselhart et al. | |
| 8,291,907 B2 | 10/2012 | Kuhlmann | |
| 8,355,769 B2 | 1/2013 | Levendowski | |
| 8,667,962 B2 | 3/2014 | Kenyon | |
| 2001/0037519 A1 | 11/2001 | Paris et al. | |
| 2002/0073479 A1 | 6/2002 | Epperson et al. | |
| 2006/0000009 A1 | 1/2006 | Fleming | |
| 2007/0251527 A1 | 11/2007 | Sleeper | |
| 2008/0047560 A1 * | 2/2008 | Veliss | A61M 16/06 128/206.24 |
| 2008/0276933 A1 | 11/2008 | Dampney et al. | |
| 2009/0032018 A1 | 2/2009 | Eaton et al. | |
| 2009/0223518 A1 * | 9/2009 | Kwok | A61M 16/06 128/205.25 |
| 2011/0186045 A1 | 8/2011 | Erickson | |
| 2013/0014751 A1 | 1/2013 | Ausen | |
| 2013/0046219 A1 | 2/2013 | Mendez et al. | |
| 2013/0133646 A1 | 5/2013 | Rose | |
| 2013/0219598 A1 | 8/2013 | Pfanner et al. | |
| 2013/0298912 A1 | 11/2013 | Gulliver et al. | |
| 2014/0137870 A1 | 5/2014 | Barlow et al. | |

* cited by examiner

CRANIUM CUDDLER

CROSS-REFERENCE TO RELATED APPLICATIONS

This application is a continuation application of International Patent Application No. PCT/U.S.2016/020735, entitled "Cranium Cuddler", filed Mar. 3, 2016, which claims priority to U.S. Provisional Application No. 62/127,628, entitled "Cranium Cuddler", filed Mar. 3, 2015 and the specification thereof is incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

One aspect of the present invention relates to a positive airway pressure support system and in particular to patient interface device for communicating a flow of air to an airway of a user in which the patient interface device includes a helmet-style headgear adapted to support an airway interface on a user and to an associated method of using such a patient interface system.

Aspects of the present invention generally relates to components for medical systems for conveying gases to and or from a patient's airway. In one particular aspect, the invention relates to headgear, a patient interface, or an assembly of headgear and a patient interface as part of a medical system for conveying breathable gases to and/or from a patient or as part of a breathing system.

Human infants are commonly described as obligate nasal breathers as they prefer breathing through their nose rather than mouth. Most infants, however, are able to breathe through their mouth if their nose is blocked. Continuous Positive Airway Pressure (CPAP) is a commonly used, noninvasive treatment for various respiratory diseases in neonates, children and adults. Nasal masks and cannula which forms (in part) a patient interface of some breathing systems, are typically held in place on a patient's head by elasticized straps, buckles or retaining systems which often include Velcro straps and tape. For example, adhesive patches or other dermal connection systems are used to position the mask and cannula onto an infant's face. The pressure applied by the straps under tension and tape placed on the face of the existing tethering systems result is distortion of facial and cranial structures, skin reactions, skin abrasions or breakdown when the adhesive is applied and removed multiple times. To overcome the deleterious effects of current CPAP tethering, an innovative medical system was implemented. The medical system comprises a helmet which offers reduced or minimal pressure on the skull or facial features (for example, cheeks) of the patient by helmet and minimizes pressure along cranial structures.

Problems with neonatal or infant CPAP and Endotracheal patient devices in use are that the devices include straps tethering a nasal cannula and bonnet/head gear to the bony structure of the face to secure the device firmly to the face. The straps used to connect the nasal cannula or mask to the face have a narrow width of about 0.75 cm at the narrow end to about 1 cm at the distal end. When the strap is in use, the strap is stretched around the head and under tension. The tension places a lot of pressure on a limited area of the face (cheeks). Often the breathing system is used by a neonate for a long period of time (months) and worn each day for many hours. There are many examples of a strap tethering system connected to a gas delivery mask and used to hold a gas delivery mask such as a CPAP mask onto the face of a patient such as a neonate wherein the same degree of (constant) pressure is exerted on a limited area of the face causing distortions to the face and resulting in facial deformities over time. This is especially problematic in neonates having deformable bones and tissues. The constant pressure delivered to the face by the small surface area of a strap or band around the head and in direct contact with a neonate's face (e.g. cheeks) in order to secure the mask or nasal cannula to the face causes the problems earlier discussed.

BRIEF SUMMARY OF THE INVENTION

One embodiment of the present invention provides a headgear for securing a patient airway interface device to a patient's head comprising a concave partial helmet having an outer surface and an inner surface and having a left lateral element, a right lateral element, a top portion and a back portion, wherein the left lateral element and the right lateral element are separated at a front half of the concave partial helmet by a void between the front half top portion of the concave partial helmet and the left lateral element and the right lateral element. When on the patient's head the top portion of the concave partial helmet terminates at the forehead of the patient's head with a front face of the top portion of the concave partial helmet that is proximal to the forehead having a stabilizer for supporting a hub. The left lateral element and the right lateral element are structured to terminate on either side of a patient's face near a cheek portion without directly touching the check portion. A section of the right lateral element and the left lateral element that is near the cheek portion includes an opening that permits passage of a strap from the outer surface to the inner surface. A portion of the inner surface of the concave partial helmet that is structured to overlay the back half of the skull when the headgear is in use is separated from the patient's head by a pliable material that is attached to the inner surface. Optionally, the top portion of the concave partial helmet includes an open portion to allow access to a fontanel area of the patient's head. The left lateral element and the right lateral element of the concave partial helmet may cover an ear and includes a removable noise abatement cover that when removed leaves an opening in the left lateral element or the right lateral element at a position over the ear. The back portion of the concave partial helmet is structured to overlay an occipital bone area of the patient's head. The left lateral element of the concave partial helmet and the right lateral element of the concave partial helmet may be moveably connected with a connector to the back portion of the partial helmet. The connector may be a hinge for example. A portion of the inner surface of the concave partial helmet that is structured to overlay a back portion of the skull when the headgear is in use can be separated from the patient's head by a pliable material that is attached to the inner surface. For example, the pliable material is connected to the inner surface releasably, the pliable material will remain in conformity with the natural shape of the head while in use. The pliable material is covered by a washable lining.

Another embodiment of the present invention is a gas delivery system adapted to provide a flow of gas to an airway of a patient, the system comprising a headgear for securing a patient airway interface device to a patient's head, the headgear comprising a concave partial helmet as described herein. A gas delivery conduit comprising a patient airway interface with an airway interface support having straps for securing the patient airway interface to the concave partial helmet at a position in relation with a patient's nostril for delivery of gas under pressures to the nostril is attached to the partial helmet. The strap is secured to the concave partial helmet via an opening in a left lateral element of the concave partial helmet and a right lateral element of the concave partial helmet. The opening is a plurality of openings at different locations on the right lateral element of the concave partial helmet and the left lateral element of the concave partial helmet used to select a best angle for securing the patient airway interface device relative to a patient's nostril. The gas delivery conduit is attached to the concave partial helmet by a hub attached to a stabilizer on a front of the concave partial helmet, the hub having an opening through which passes the gas delivery conduit at an angel to the hub which allows the patient airway interface device positioned at a first end of the gas delivery conduit to be immediately adjacent to the nostril of a patient wearing the concave partial helmet. The gas delivery conduit at a second end extends above the hub. An eye patch may be tethered to the concave partial helmet when the patient is in need thereof.

Another embodiment provides for a method of securing a patient airway interface to a patient's head comprising the steps of attaching a conduit for carrying gas under pressure to a patient wearing a headgear as described herein wherein the conduit has a first end and a second end wherein the first end is a patient airway interface that provides gas under pressure to a nostril of a patient when the patient airway interface is adjacent to the nostril and the second end extends above a hub attached to a top portion of a concave partial helmet as described herein when positioned on the head of a patient. The patient airway interface is secured adjacent to the nostril of a patient with a strap positioned around the concave partial helmet and attached to the patient airway interface at an angel to hold the patient airway interface in place adjacent to the nostril to deliver gas under pressure to the nostril of the patient. The conduit at its second end attaches to a hose for carrying gas under pressure. A strap passes from the interior side of the helmet to the exterior side of the helmet through an opening in a lateral element of the helmet wherein the strap rests on the outside of the helmet after passing through the opening. The patient airway interface is positionable up or down, side to side and toward or away relative to the nostrils.

One aspect of an embodiment of the present invention provides for a helmet placed onto the skull of the patient. The helmet which partially covers the skull and includes a side lateral element on the helmet which acts as a base to which is connected a strap which holds in place the mask or nasal interface used to supply gas to the patient. In contrast to prior art, the strap holding the mask onto the face is no longer positioned around the skull exerting pressure on the skull and directly against the skull to pull the mask onto the face but instead the strap is secured to the helmet via a side lateral element of the helmet or stretched around the helmet when the strap is used to secure a mask or nasal interface onto the face of the patient. Therefore, the helmet acts to relieve the pressure directly exerted by the strap under tension onto the skull and face when in use. The helmet is used for example with a neonate to reduce pressure on cranial structures and to support a gas delivery conduit in the proper position for gas delivery to the airway of the patient for example the nostrils.

Another aspect provides for a helmet with minimal pressure on the skull or cranium structures as the rigid structure of the helmet does not directly touch the maxillofacial area.

Another aspect provides a CPAP patient device for reduction of pressure on major pressure points on the head as compared to a prior tethering system where a strap under tension is stretched around the head of the patient to hold a CPAP mask in place on the face of the patient.

Another aspect of an embodiment of the present invention provides for a helmet with a hinge on a side lateral element that connects the lateral element to the back of the helmet. The lateral element wraps around the skull from the back portion of the helmet and wraps over a portion of the temporal bone when the helmet is in use on a patient. The lateral element is sometimes referred to herein as a side wing of the helmet. The hinge connects each of the side wings to the back portion of the helmet and allows the side wings to expand outward relative to the back portion of the helmet for easy removal from and placement on the patient's head.

Another aspect provides for a deformable cushion liner inside of the helmet to cushion the head and to adapt to the shape of the infants head. The cushion may be for example viscoelastic polyurethane foam such as memory foam with or without liquid-proof silicone elastic or padding of any type.

Another aspect of an embodiment of the present invention provides for a removable/washable cotton pad lining attached to the interior surface of the helmet.

Yet another aspect provides for infant weight ranges for the helmet of between about 500 g-1000 g and 1000 g-1500 g to accommodate head growth without the helmet causing excessive pressure and larger size helmets can accommodate head size of larger children and adults.

Yet another aspect provides a helmet that expands with head growth without causing distortion.

Another aspect of the present invention provides a helmet which may only cover sections of the side and back and top of the patient's head and/or having an exposed area of anterior fontanel for the application of an ultrasound probe.

One aspect of an embodiment provides for a hole (sometimes referred to herein as slit) in a side wing for example—multiple holes/slits are provided to determine the best angle at which to place the tethering strap connected to the mask or patient airway interface in relation to the nose of the patient and/or the patient airway interface or mask and choose the optimal tethering force as seen in Table I. The holes may also be used to fix eye patches in a desired position overlaying the eyes of the patient during phototherapy while minimizing or removing pressure on the patient's checks caused by the eye patch straps extending around the head and stretching over the checks in order to secure the eye patch in place. Ear covers for noise reduction may be removably attached to the side wing ear holes or openings. Another embodiment provides for the use of a cleat or a tethering rod with notches on the helmet for securing the tethering strap or eye patch strap to the helmet. Alternatively, Velcro on the helmet could interact with the tethering strap for securing the strap and the attached mask in proper place on the face. The side lateral element wraps around the side of the head and covering a portion thereof (temporal bone, mastoid process, and maxilla facial area) and over the patient's ears, with minimal visual restriction to the patient.

Another aspect of the present invention is that the helmet and lining may be made of biocompatible, hypoallergenic material. Yet another aspect of the present invention provides for no measurable moisture retention of the lining and/or helmet and ability to access the head for EEG's. An additional aspect of an embodiment of the present invention provides for a patient airway interface system that maintains natural curvature of baby's head.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

As used herein "a", "an" or "the" means one or more unless otherwise defined.

As used herein "patient" means neonate, infant, child or adult.

Figure 1:
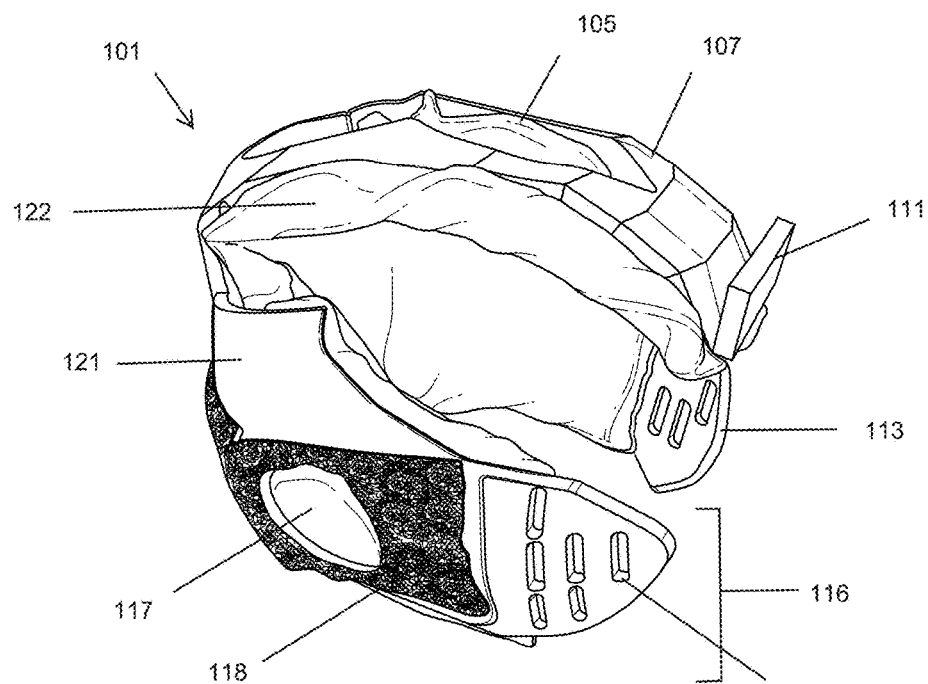
FIG. 1 is right side view (from perspective of the wearer) of the helmet with interior cushion according to one embodiment of the present invention.

Referring now to FIG. 1, an embodiment of a helmet 101 is illustrated. The helmet has a concavity at a top portion 107, a back portion 121 and a right side lateral element 116 and a left side lateral element 113 that sometimes is referred to herein as a side wing of the helmet. The helmet concavity is designed to cradle the head of the wearer. The helmet at least partially covers the top, back and side of the skull of a patient and conforms to the normal contour of a patient's skull/cranium while leaving the face mostly exposed. In one embodiment, the helmet does not fully cover the patient's skull. The helmet is manufactured of a rigid outer shell, for example, ABS. There is a cushion 122 that separates the rigid outer shell of the helmet from contacting the face. The cushion 122 may include a cloth lining covering a pliable material that deforms when pressure is applied such as the pressure from the weight of a patient's head resting on an interior surface of the helmet. In this embodiment, the helmet does not entirely cover the frontal, parietal and occipital areas of the skull. In one embodiment, the back portion is designed to cover a center back portion of the head and extend over the top of the infant's head. The front top portion of the helmet ends at the upper forehead of the frontal bone. The front edge of the front top portion includes a stabilizer 111 upon which a conduit carrying fluid such as a gas will rest and/or be secured via a conduit holder (not shown) which can attach to the stabilizer. In one embodiment the stabilizer 111 extends upward and/or downward from the front edge of the top portion. A lateral side element extends around each side of the helmet. The lateral side element may be of the same rigid material that makes up the back portion of the helmet or different. When the helmet is on the head of the patient, each lateral side element curves around from the back side of the helmet and extends around the front of the face over at least a portion of the zygomatic bone of the patient without the rigid shell of the lateral side element directly touching the patient when the patient is lying in the supine position. The top portion of the helmet may have an opening 105 through which the top of the head can be accessed. There is an open space between the top portion of the helmet and the lateral side element. There is an opening/slit 119 in one or both of the lateral side elements for example at the front portion of the lateral side element. Ear opening 117 is located in each lateral side element of the helmet. The ear opening can be covered to protect the patient's ears from noises.

Figure 2:
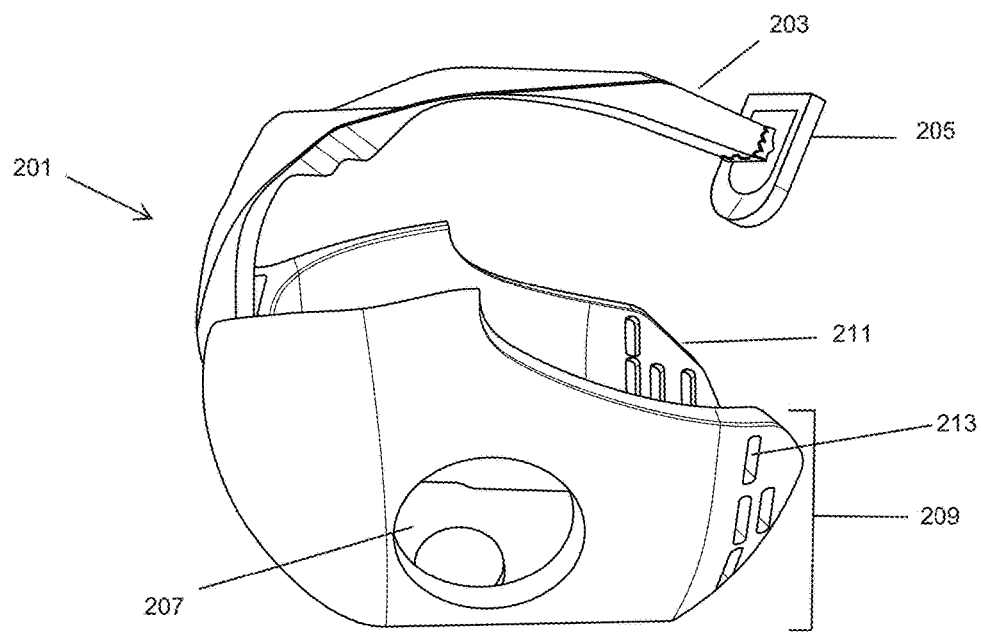
FIG. 2 is right side view of the helmet of FIG. 1 without the cushion.

Referring now to FIG. 2 is a right side view of a helmet 201 according to one embodiment of the present invention. The right lateral side element 209 is illustrated with a cutout 207 which is positioned over the ear when the helmet is worn by the patient. The opening can be obstructed with pads to abate noise from the environment in which the patient is placed. Openings 213 are positioned at the front end of the first lateral side element for tethering a strap used to support a mask or nasal cannula onto the face of a patient. The stabilizer 205 can be shaped to extend above and below the front edge of the top portion 203 of the helmet. The ear opening 207 can be covered to protect the ears as required.

Figure 3:
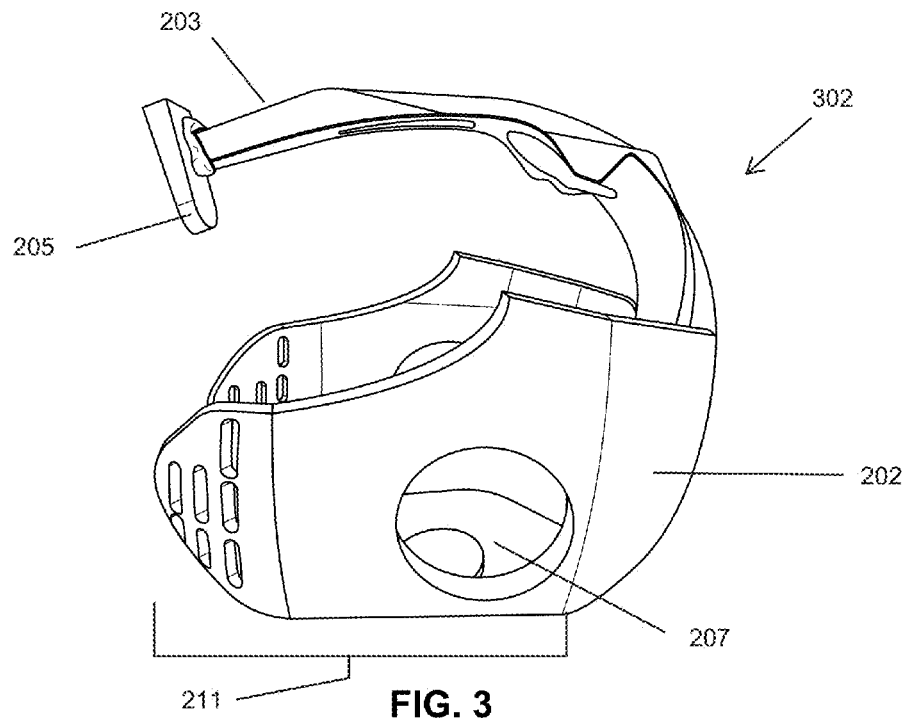
FIG. 3 is a left side view of the helmet of FIG. 2.

Referring now to FIG. 3, is a left side view of the helmet of FIG. 2 is illustrated according to one embodiment of the present invention. The left side view is identical to the right side view in this embodiment but is not limited thereto as each side may be engineered to have a unique feature (more cushioning, for example, or no ear opening).

Figure 4:
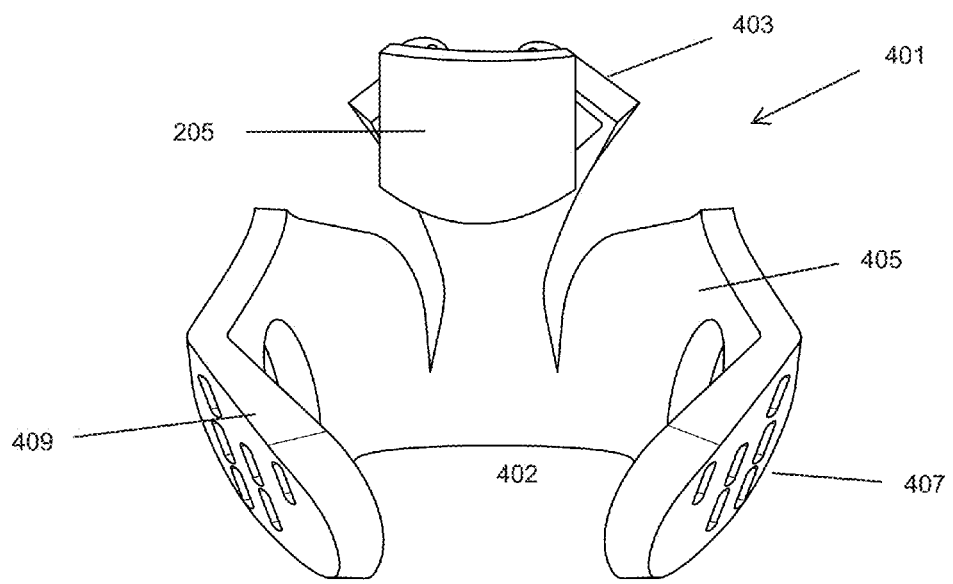
FIG. 4 is a front view of the helmet of FIG. 2.

Referring now to FIG. 4 is a front view of a helmet according to one embodiment of the present invention. The helmet 401 has a top portion 403 which has a stabilizer 205 at the front edge. The stabilizer has a surface area facing the front of the helmet is greater than the edge of the front end of the top portion of the helmet. Reference to a right side and a left side of the helmet are relative to the patient's perspective when the helmet is in use on a patient. The right lateral element and the left lateral element may be the same or different.

Figure 5:
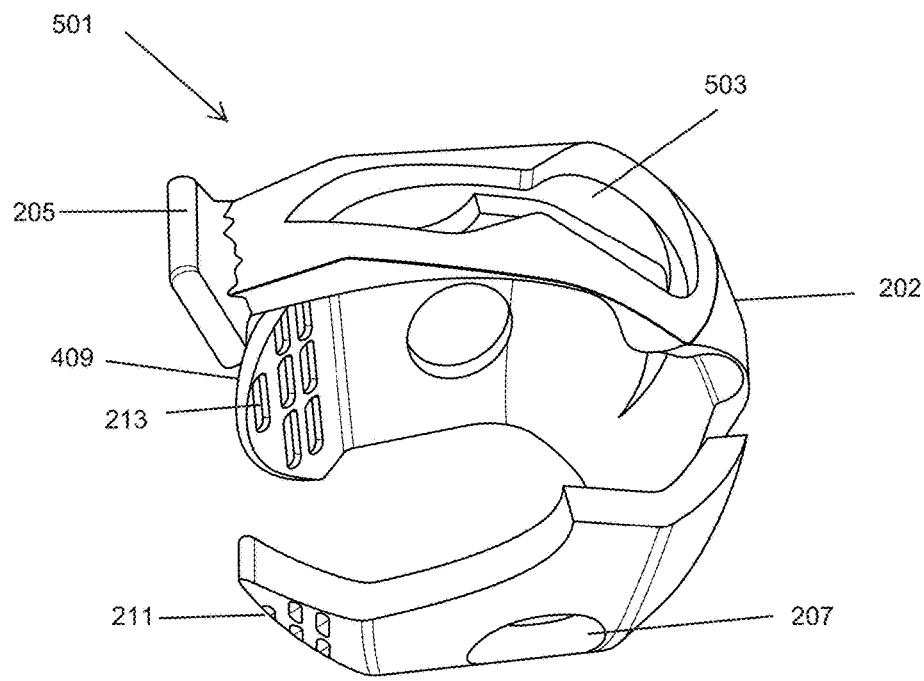
FIG. 5 is a perspective view of the left side of the helmet of FIG. 2.

Referring now to FIG. 5, a perspective view of helmet 501 of FIG. 2 is illustrated according to one embodiment of the present invention. The helmet as illustrated exhibits a rigid outer shell/exoskeleton that is concave and can be made of a plastic such as ABS filament. The top portion of the helmet has an opening 503. The back side of the helmet 202 connects with the lateral side elements 211 and 409.

Figure 6:
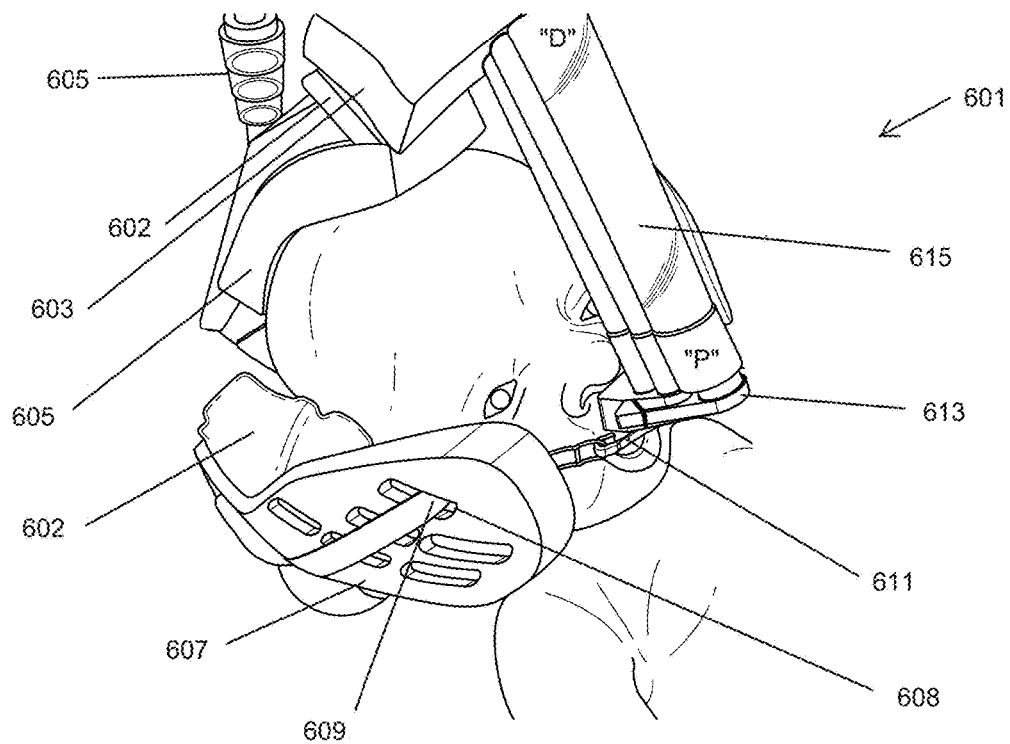
FIG. 6 is a view of a patient wearing the helmet assembly according to one embodiment of the present invention.

Referring now to FIG. 6, a helmet 601, according to one embodiment of the present invention, is illustrated positioned snuggly on the head of a patient that is a neonate. The patient airway interface 613 extends to the nostrils of the nose from a conduit 615. The conduit at the distal end "D" is held away from the face by the stabilizer 602, and the patient airway interface at the proximal end "P" of the conduit is supported by an airway support 611 which positions the patient airway interface 613 in proper position with the neonate's nostrils for gas to flow into the nostrils of the neonate from the conduit. The stabilizer rest connects with a hub 603. The conduit passes through an opening in the hub. The hub supports the conduit as it passes down from above the top portion of the helmet. The hub holds the conduit a distance away from the forehead of the patient and permits the conduit to be positioned at a distance from the front of the patient's face and prevents the upper portion of the conduit extending from the bottom portion of the hub from touching the neonate's face at the forehead. The conduit is in contact or in close proximity with the nose/nostril of the neonate at the distal end of the conduit through a patient airway interface 613, for example. Alternatively the conduit is in contact with the mouth when the system is used to pass fluids to and from the stomach for example through an endotracheal tube. A strap 609 is positioned from around the side of the helmet and passes through slit/opening 608 in the front portion of the lateral side element to position the patient airway interface at a distance at the proper position relative to the neonate's face/nostrils. The patient airway interface rests on the airway support strap 611 that passes under the end of the conduit and between each side wing. The patient airway interface 613 directs gas to the neonate's nostrils. Further, the helmet is open at the top portion to implement access for anterior fontanel ultrasound. The helmet permits proper CPAP function and effective tethering and could support an endotracheal tube. The helmet includes padding 605 that separates the rigid helmet from the skull and facilitates a snug fit. If padding is moist and in a warm environment it can breed bacteria. Often secretions end up on pillows, and nurses need easy access to clean them. Therefore detachable pads can be included for complete disposal of padding and replacement. Alternatively a layer of silicon between the memory foam and the cloth can be added as a protective layer that can be wiped down with only the cloth covering the pad to be changed.

Figure 7A:
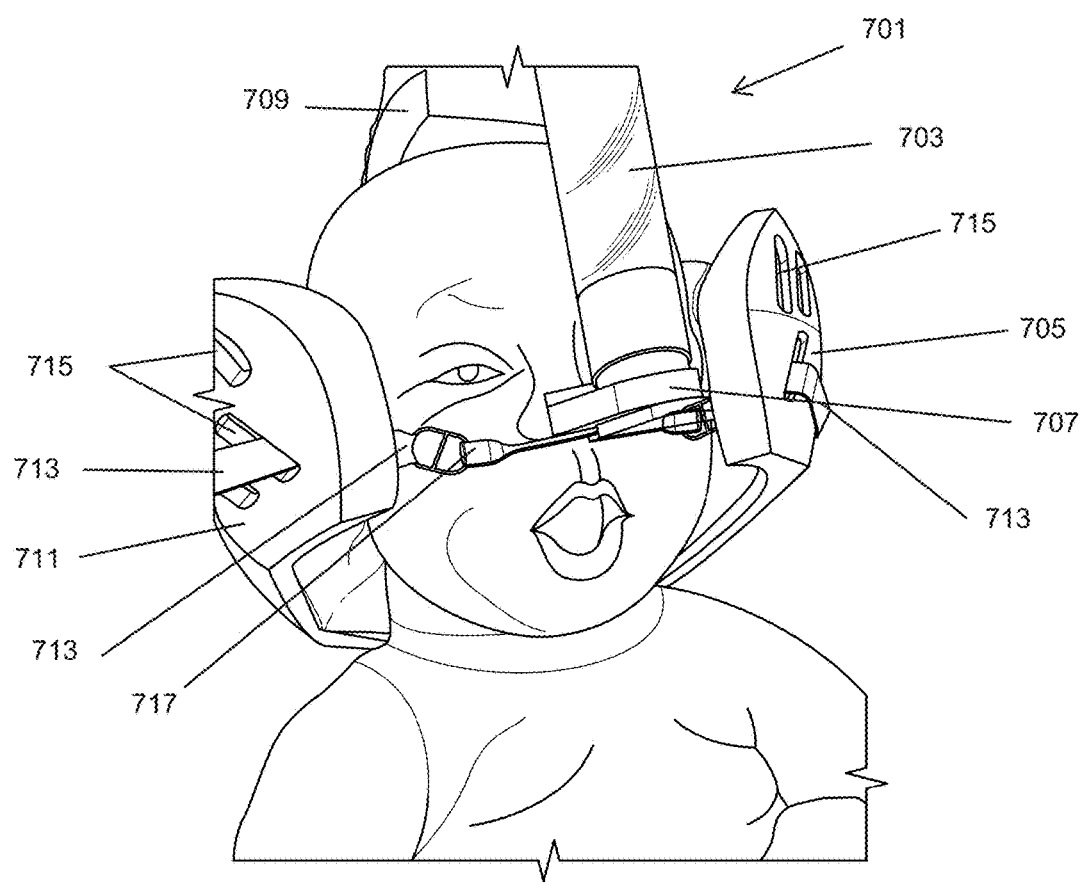
FIGS. 7A-C, is an illustration of a patient wearing the helmet according to one embodiment of the present invention.

Referring now to FIG. 7A, the helmet assembly system is illustrated positioned on the head of a patient. Assembly 701 includes a conduit 703 that is supported at the distal end by stabilizer 709 and supported by airway support 717 at the patient airway interface 707 at the proximal end. The airway support 717 is attached to strap 713 on either side of the conduit. Strap 713 passes through one of the multiple openings 715 on the right side lateral element 711 and the left side lateral element 705. The strap can extend around the back of the helmet when the strap is one piece with ends that connect to the right and left ends of the airway support 717. Alternatively the right side strap and the left side strap attach or anchor to the helmet itself and do not require stretching the strap around the backside of the helmet to put tension on the strap to keep the patient airway interface positioned at a distance from the face to support the patient airway interface 707 in contact with the nostrils.

Figure 7B:
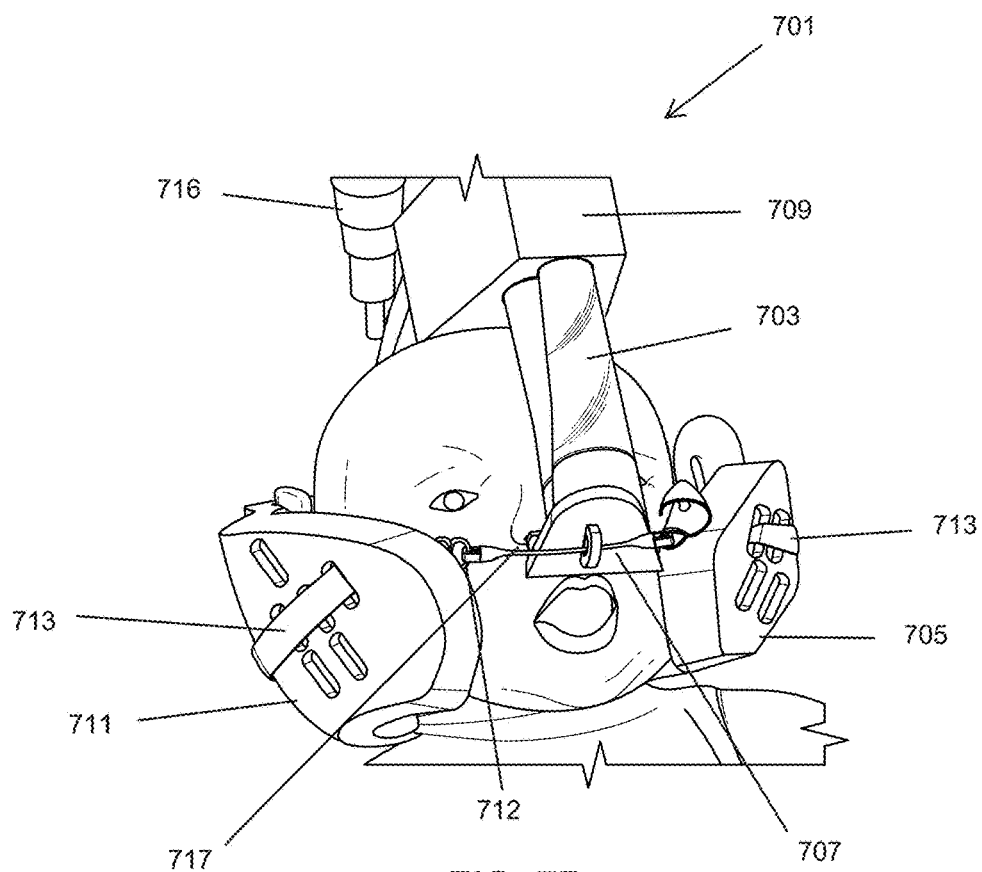
Figure 7C:
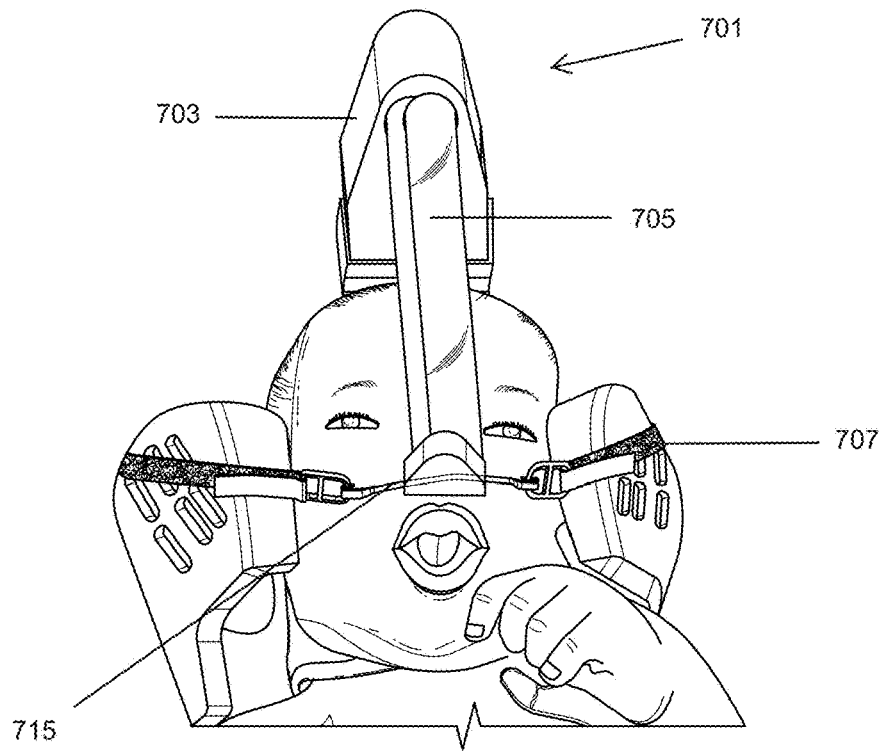

Referring now to FIG. 7B, the helmet assembly 701 is illustrated showing the airway support 717 for the patient airway interface 707 positioned through a guide at the lower surface of the patient airway interface. The right end and the left end of the airway support attaches to an end of the strap 712 that is passed from the outside of the helmet to the inside of the helmet through an opening of the right lateral element and the left lateral element. The strap is secured to the helmet to exert tension on the strap and to position the airway support at a distance from the face below the nose to stabilize the conduit and the patient airway interface for gas to pass into the nares efficiently. A gas delivery hose 716 for example the type used with CPAP passes over the top portion of the helmet and connects with the top portion of the conduit that extends beyond the top surface of the hub/guide 709 which is attached to the stabilizer. Referring now to FIG. 7C, the helmet assembly system 701 illustrates another embodiment wherein the straps 707 which are connected to the patient airway interface support 715 do not pass through an opening of the lateral element but instead are positioned on the outside of the helmet.

Figure 8:
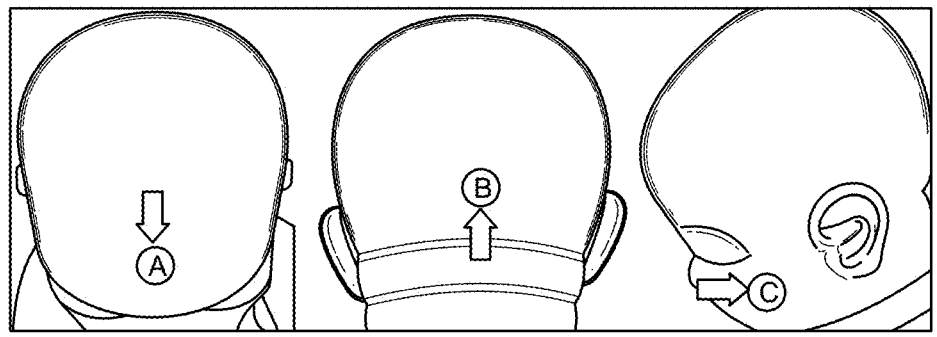
FIG. 8 is an illustration of functional analysis and pressure point comparison produced from the helmet according to one embodiment of the present invention and a prior art tethering systems.

Referring now to FIG. 8, pressure points at locations A (forehead of the frontal bone location of the skull), B (center back of the occipital bone location of the skull), and C (check area of the zygomatic bone of the skull) of a neonate were measured with a helmet according to one embodiment of the present invention when in position on a life sized neonate. The pressures at each point are shown in Table I. The pressure at the locations identified were measured for a tethering system holding a mask onto the face without a helmet and compared to the pressure at the location identified when the helmet was on the doll. There is minimal pressure at the locations identified when the helmet is in position on the head of the doll in contrast the pressure at the location identified when the tethering system is on the head of the doll.

TABLE 1

| Measurement points | Current tethering pressure | CPAP Helmet |
|---|---|---|
| A | 5.90460 | 0.0000 |
| B | 4.997270 | 0.04127 |
| C | 5.14279 | 0.0000 |

Figure 9:
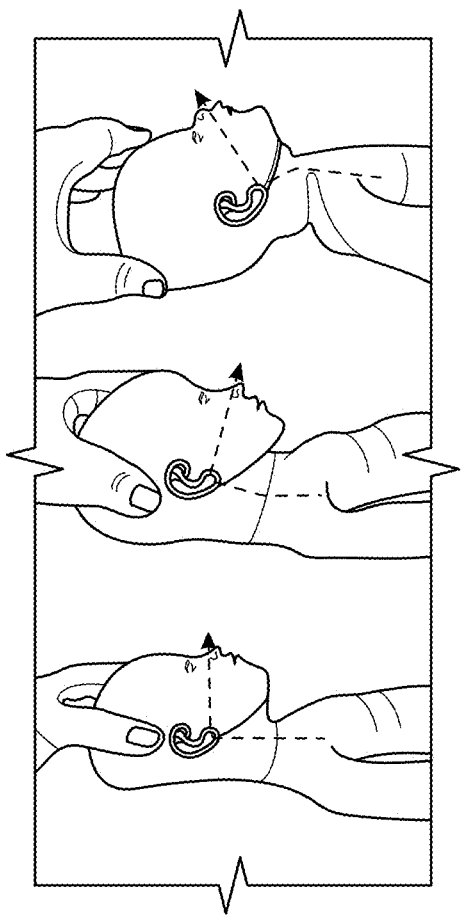
FIG. 9 is an illustration of neck positioning of a neonate for optimal airway position.

Referring now to FIG. 9, a neonate's neck position dramatically affects airflow through the trachea. It is important that the head is aligned as best as possible. The helmet promotes correct neck alignment to facilitate unimpaired airflow through the trachea. Neonates have few head positions that allow for unimpaired airflow through the trachea. It is important to keep the head aligned as best as possible. By placing a small roll of cloth under the neonate's neck it prevents flexing. The degree of flexion for positioning may be adjusted by padding or cushions positioned on the lower edge of the back portion of the helmet.

Figure 10:
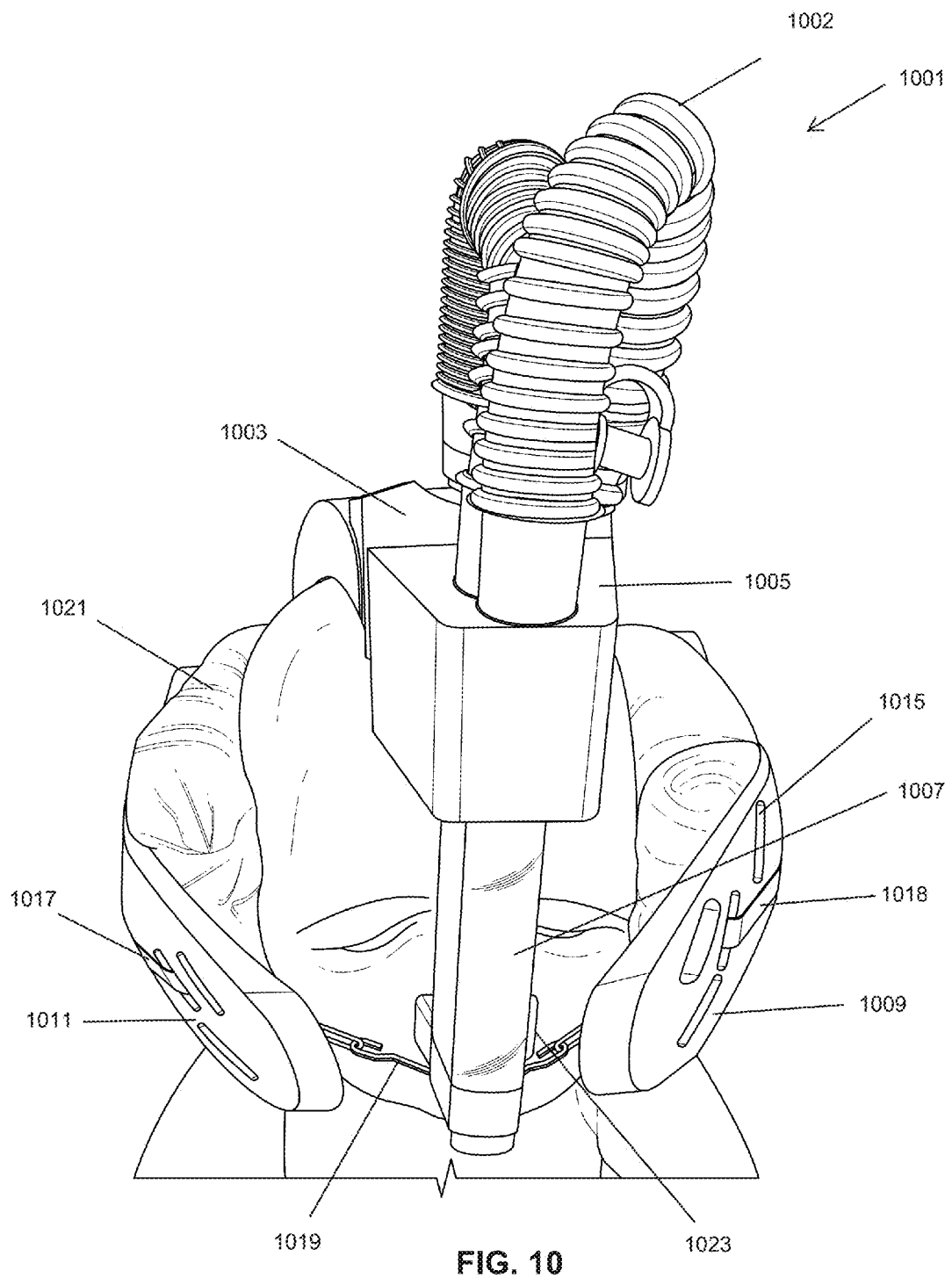
FIG. 10 is an illustration of a front view of the helmet assembly on a patient according to one embodiment of the present invention.
Figure 11:
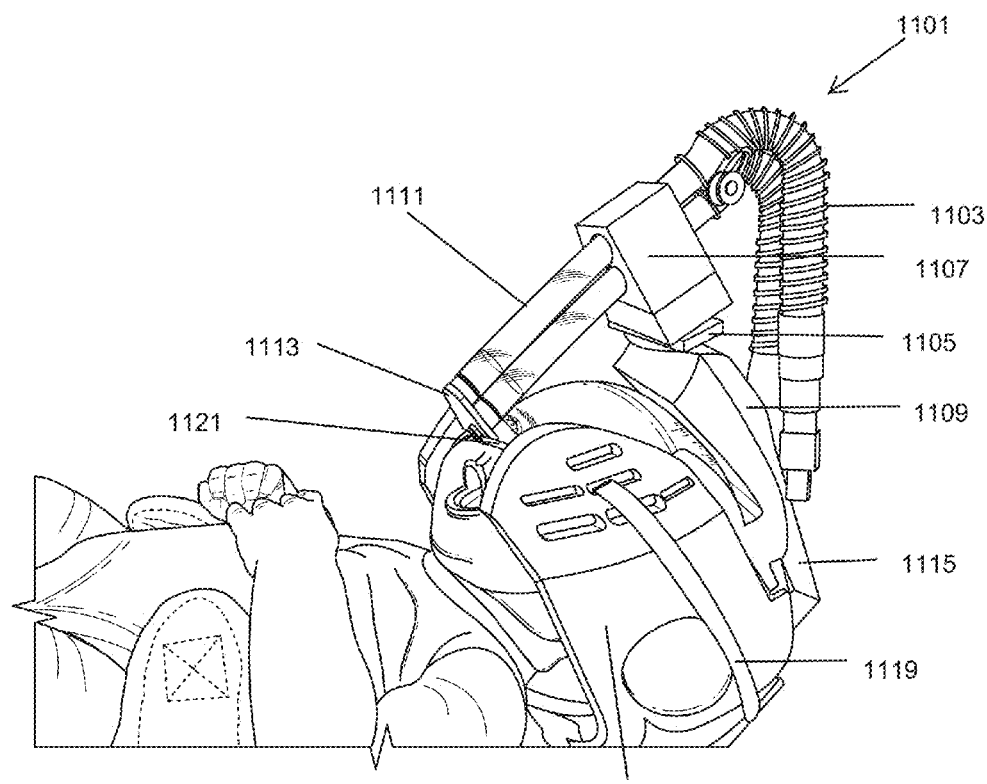
FIG. 11 is an illustration of a side view of the helmet assembly with the patient airway interface resting on an airway support tether/connector.
Figure 12:
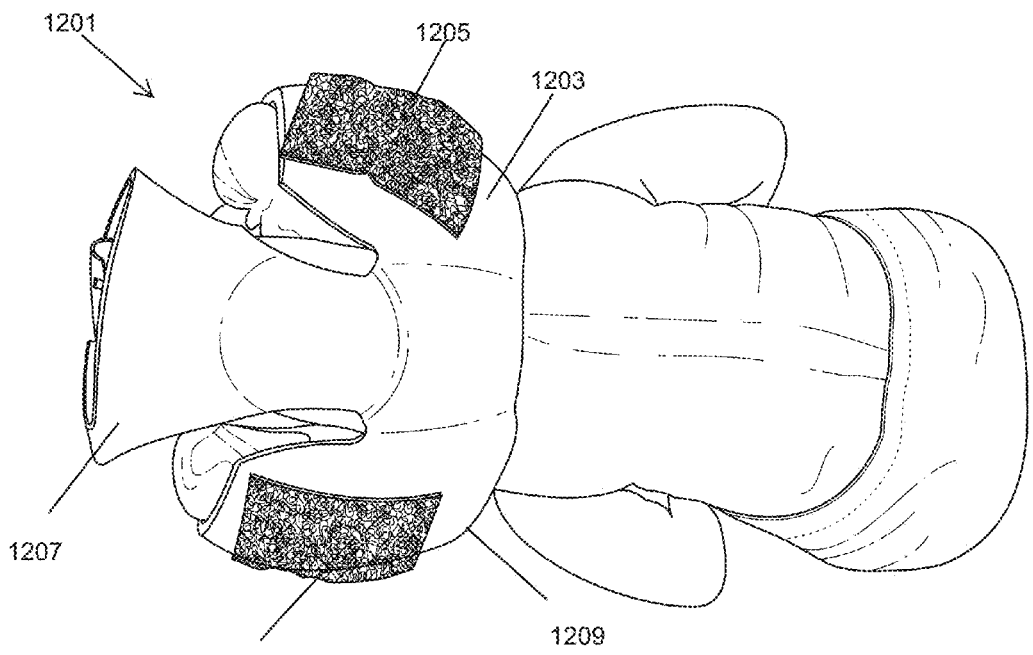
FIG. 12 is a back view of the helmet on a patient according to one embodiment of the present invention.

Referring now to FIG. 10, a helmet assembly 1001 is illustrated wherein the hose for carrying gas 1002 attached to the top of the conduit which hose 1002 passes down from above the helmet through a guide/hub 1005 attached to the stabilizer 1003. The conduit is positionable relative to the neonate's nostrils by moving the conduit up or down (craniocaudal) through the guide/hub. The distal end of the conduit is the patient airway interface which can be positioned over the neonate's nostrils and secured in that position by resting the distal end of the conduit on the airway support 1019 that is secured to the sides of each lateral element 1011 and 1009 of the helmet with a strap 1017. The strap 1017 passes from the outside of the helmet through an opening or slit in a side of the right lateral element to the inside of the helmet. The strap connects to the right end of the patient airway interface support. The left strap 1018 passes from the outside of the helmet through a slit in the left lateral element and connects to the left end of the patient airway interface support. The strap 1017 and 1018 is secured to the outside of the helmet. The anterior to posterior position of the patient airway interface relative to the nostrils and the side to side position of the patient airway interface relative to the nostrils and the cranio-caudal position of the patient airway interface relative to the nostrils can be adjusted by adjusting the length of conduit that passes below the hub and the tension applied to the straps that result in the force pulling the patient airway interface in the posterior direction and into the face and against the nostrils. In a preferred embodiment, there is sufficient tension applied to the straps to hold the patient airway interface in a position at the nostrils. FIG. 11-FIG. 12 shows the helmet at a side view and a back view respectively. FIG. 11 illustrates a gas hose 1103 positioned above the top portion 1109 of the helmet. For example the gas hose could be connected to a device that facilitates breathing such as a CPAP or delivers oxygen of varying concentration. The position of the strap 1119 position on the helmet and securing the patient airway interface 1113 via the patient airway interface support 1121 is illustrated in this side view. FIG. 12 illustrates a back view of the helmet wherein straps or eyepatches for example are anchored to the helmet via for example Velcro 1205. The Velcro 1205 may be positioned on the outside of the helmet for use in attaching the straps. Hinge 1209 is positioned at the back of the helmet and the lateral elements and can help to expand the lateral elements when positioning the helmet on or off the patient. The top portion of the helmet 1207 extends to the front of the head and ends at the forehead of the frontal bone.

Figure 13:
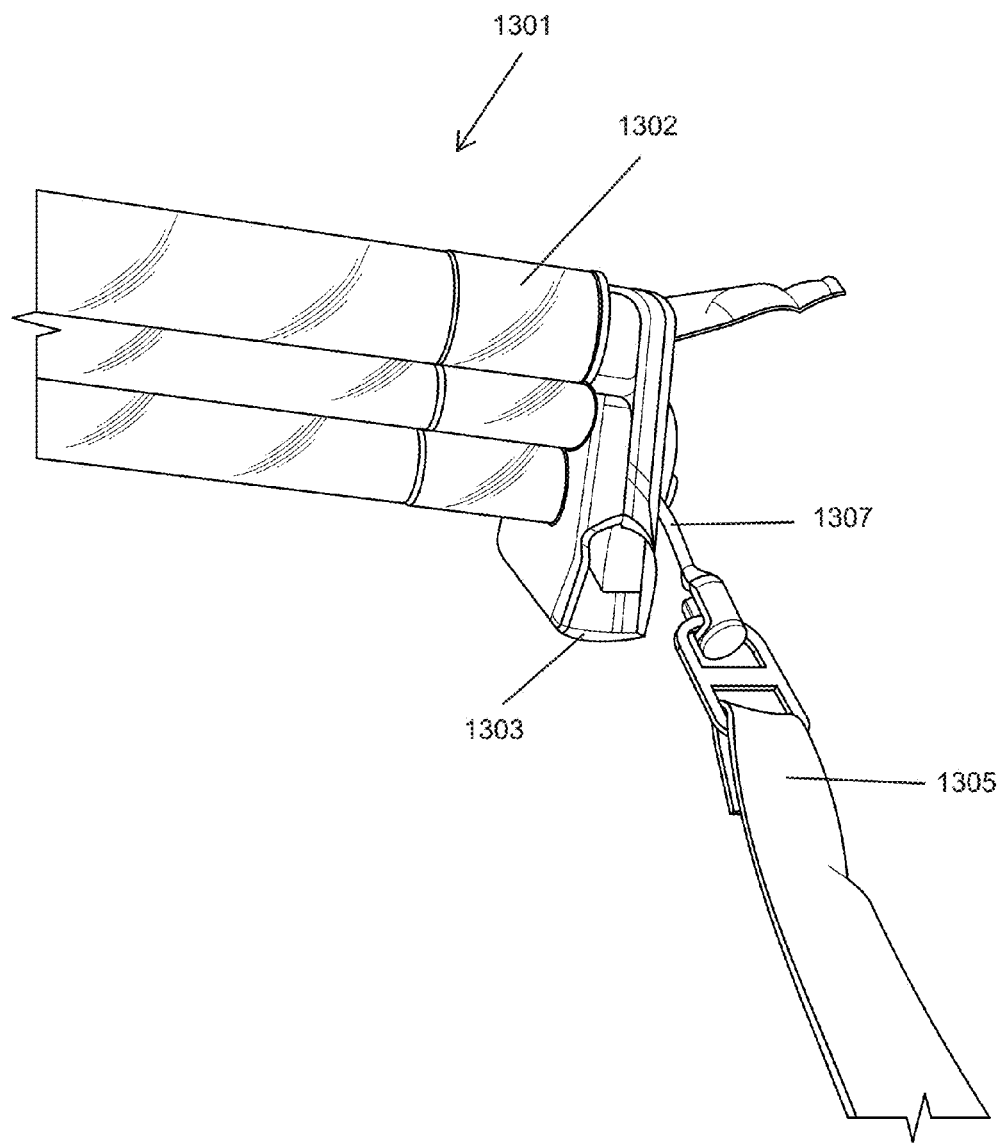
FIG. 13 is view of the prior art strap, patient airway interface and airway interface tether that attaches to the helmet.

Referring now to FIG. 13, the conduit 1301 and the airway support and strap assembly 1307 and 1305 is illustrated according to the prior art. The opening of the patient airway interface 1303 allows the patient airway interface to be positioned at the nostrils or almost toughing the tip of the nose.

Figure 14A:
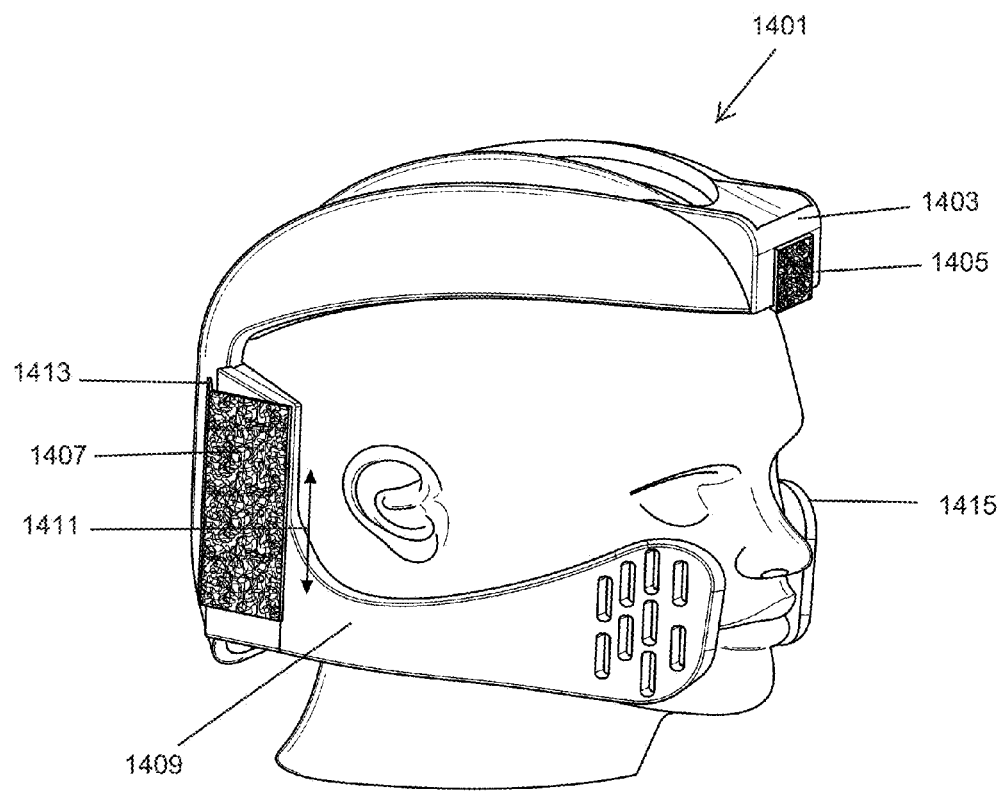
FIG. 14A and FIG. 14B illustrate another embodiment of a helmet wherein the lateral side element does not cover the ear.
Figure 14B:
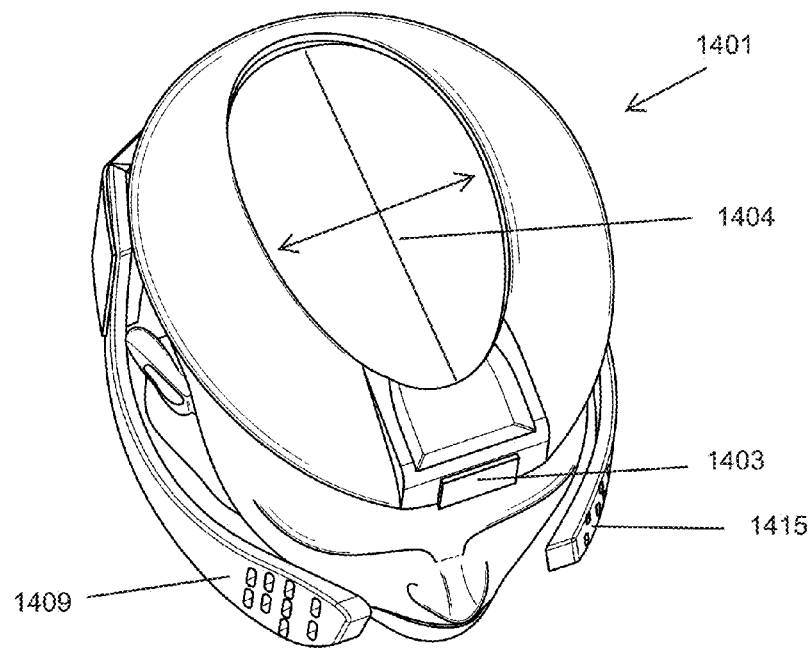

Referring now to FIG. 14A, a helmet 1401 according to another embodiment of the present invention is illustrated. The stabilizer 1403 has an attachment means such as Velcro 1405 on the front surface of the stabilizer. A hub can be positioned against the Velcro for positioning the conduit. The left lateral element 1415 and the right lateral element 1409 wrap around the face and allow the ears to be exposed as compared to other embodiments disclosed herein wherein the lateral side element may cover the ear if there is no ear opening. The lateral side elements are positionable in the direction of the arrow 1411. The hinge 1413 permits the lateral elements to be adjustable for positioning the helmet on and off the head. Referring now to FIG. 14B, a top view of helmet 1401 is illustrated. There is an open area 1404 which may be oval but is not limited thereto as any open geometry is acceptable. The right lateral element 1409 and the left lateral element 1415 curve around the front of the face and do not touch the front of the face.

Figure 15A:
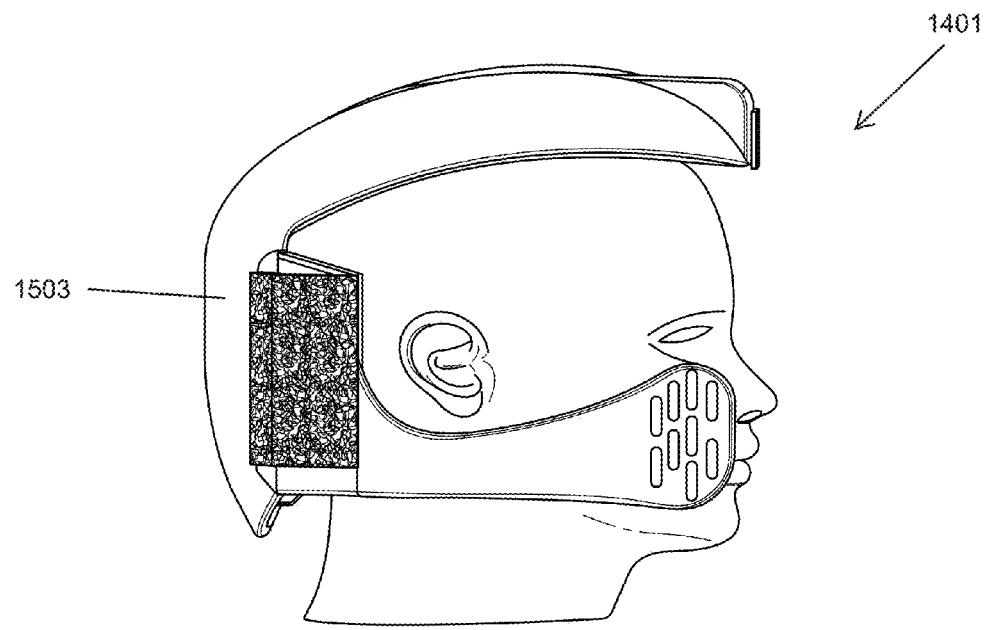
FIG. 15A and FIG. 15B provide additional views of a helmet according to FIG. 14A.

Referring now to FIG. 15, a helmet 1401 is illustrated. The curved back portion 1503 is shown in this view. The helmet partially overlays the occipital bone "O", parietal bone "P", frontal bone "F" while the lateral elements overlays the zygomatic bone "Z" and part of the temporal bone.

Figure 15B:
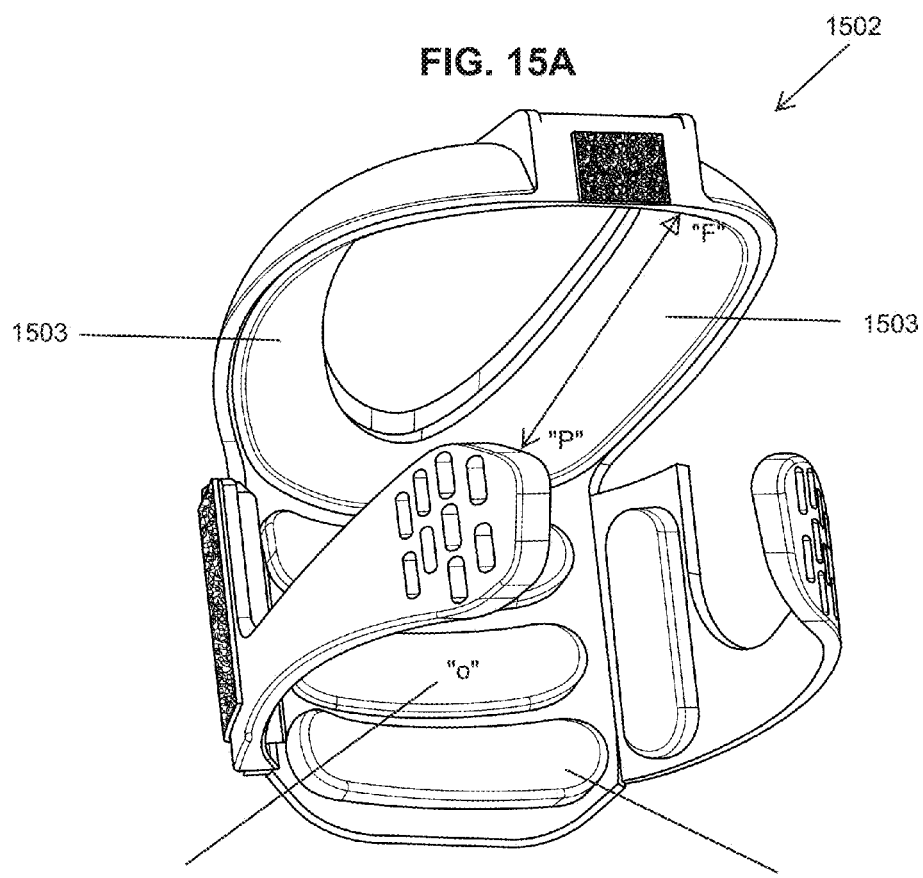

Referring now to FIG. 15B, an inside view 1502 of helmet 1401 has a pad liner 1503 in the interior. Foam pads 1505 are positioned against the inside back portion of the helmet. The lower section of the helmet is positioned over the occipital area of the skull when in place on the head of a patient. The interior top portion is designed to overlay the parietal "P" and the frontal "F" areas of the skull when in place on the patient. Notice padding of 1505 can alter the angle of flexion of the head.

Figure 16A:
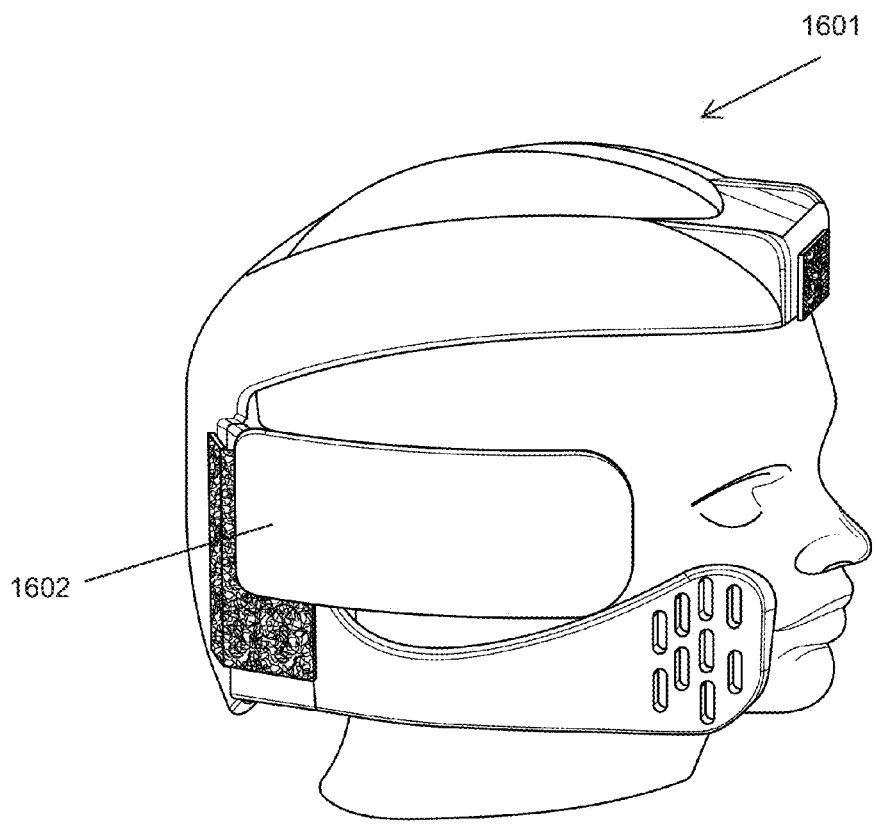
FIG. 16A and FIG. 16B illustrates the helmet of FIG. 14A with ear flap or eye mask attached according to one embodiment of the present invention.
Figure 16B:
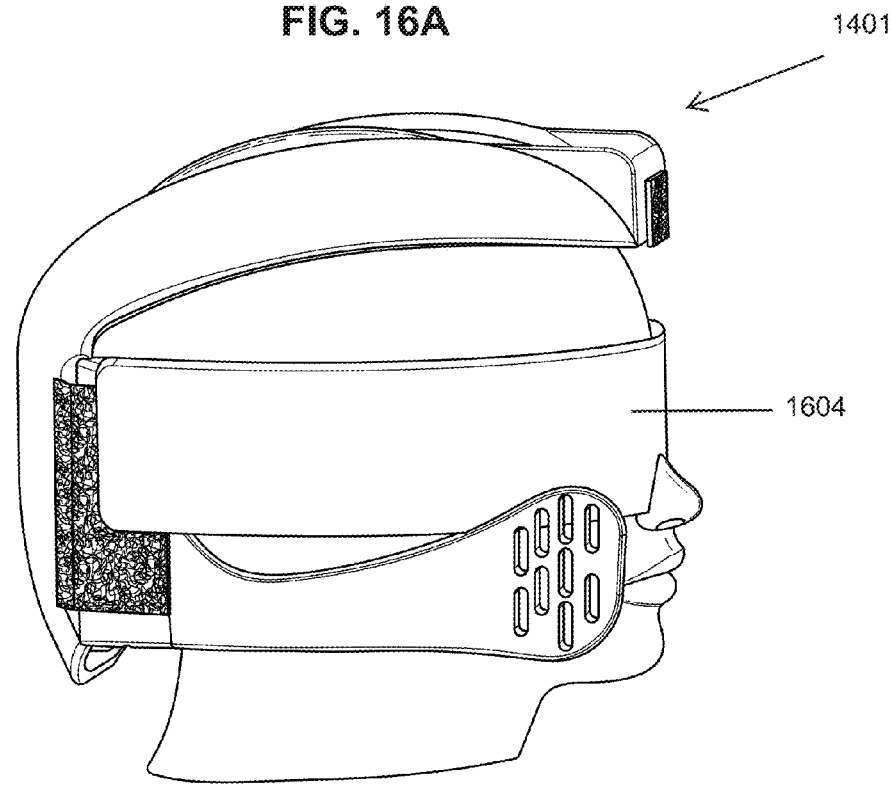

Referring now to FIG. 16A, a side view of helmet 1401 is illustrated with removable ear cover 1602. Referring now to FIG. 16B, a side view of 1401 with removable eye cover 1604 is illustrated.

Figure 17:
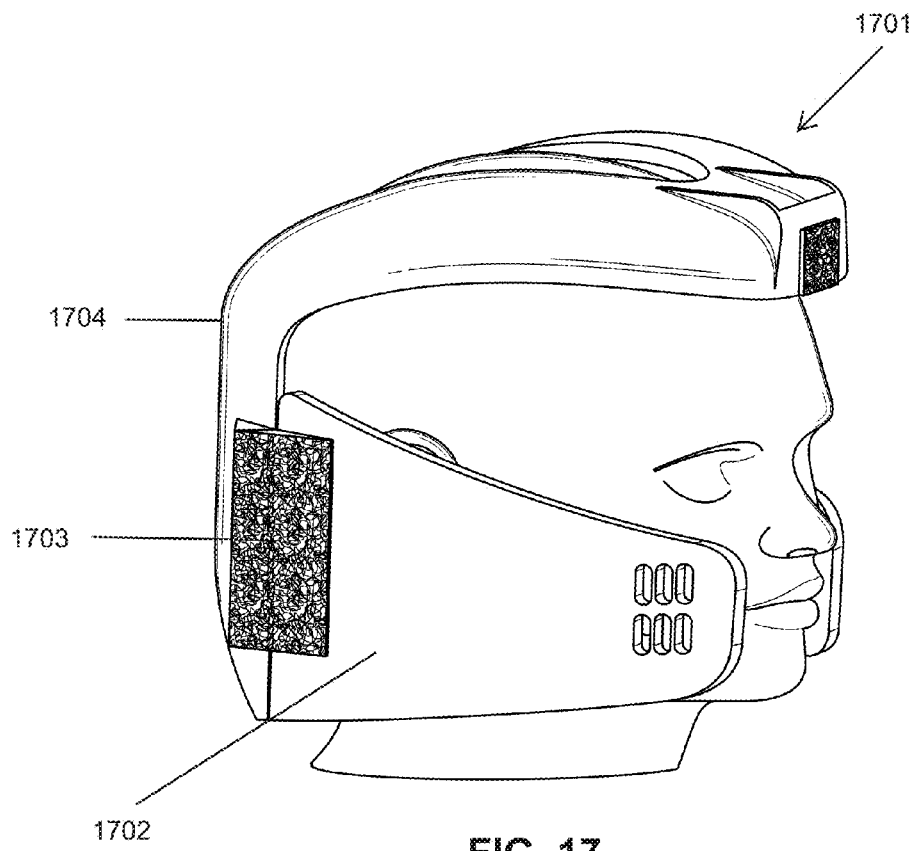
FIG. 17 is another embodiment of a helmet wherein the side lateral element covers the ear.

Referring now to FIG. 17, a helmet 1701 according to one embodiment of the present invention is illustrated wherein the lateral side element 1702 is shown to overlay a larger portion of the skull in the area of the temporal and zygomatic bones as compared top side lateral element 1409 and 1415 of FIG. 14. A hinge 1703 allows side lateral element 1702 to move outward relative the back portion 1704 of the helmet.

Figure 18:
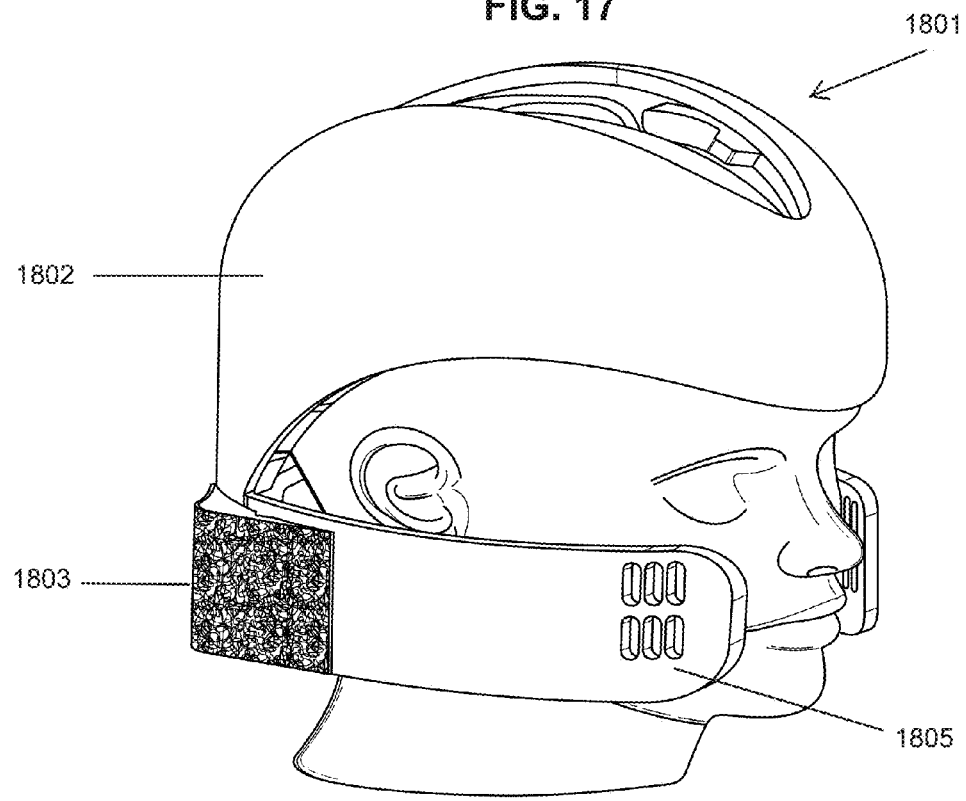
FIG. 18 is another embodiment of a helmet wherein the top portion covers a larger portion of the skull.

Referring to FIG. 18, a helmet 1801 according to another embodiment of the present invention is illustrated. The top portion 1802 covers a larger section of the frontal and parietal bones of the skull as compared to other embodiments of the invention described herein. An opening exists in the top portion for access to the head at the frontal portion of the skull.

Figure 19:
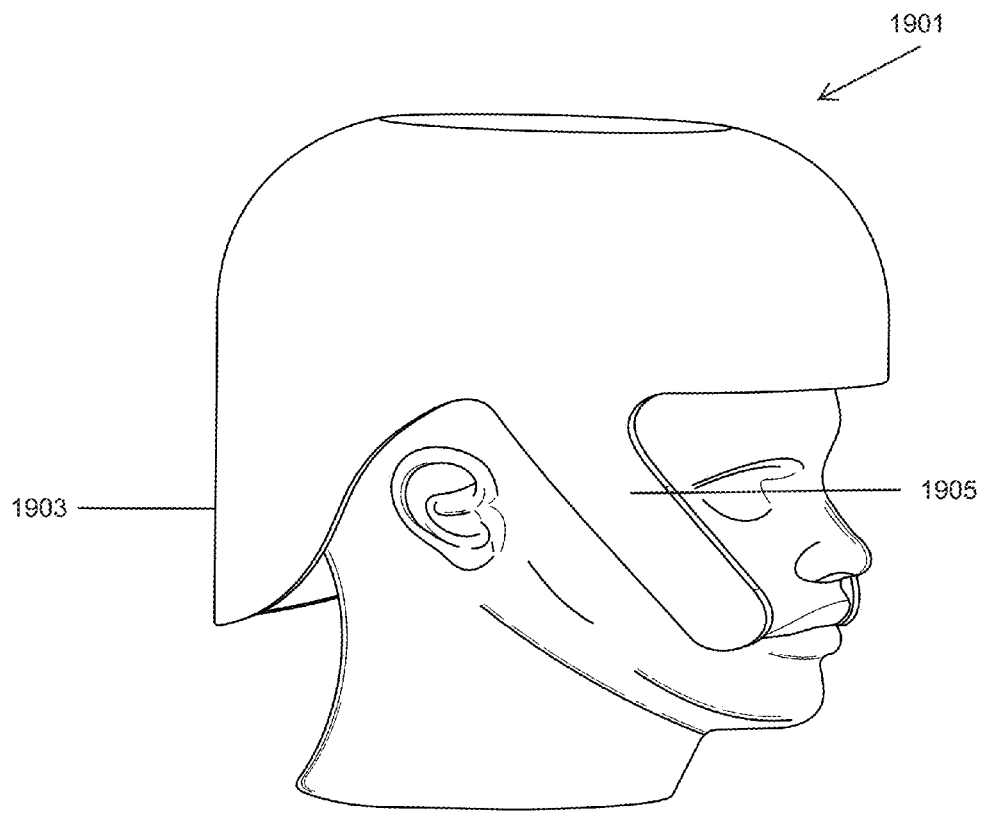
FIG. 19 is another embodiment of a helmet wherein the side lateral element extends from the top portion of the helmet.

Referring now to FIG. 19, a helmet 1901 is illustrated wherein the lateral side element 1905 extends from the top portion of the helmet. The helmet is not curved at the back portion 1903 that overlays the occipital bone.

Figure 20:
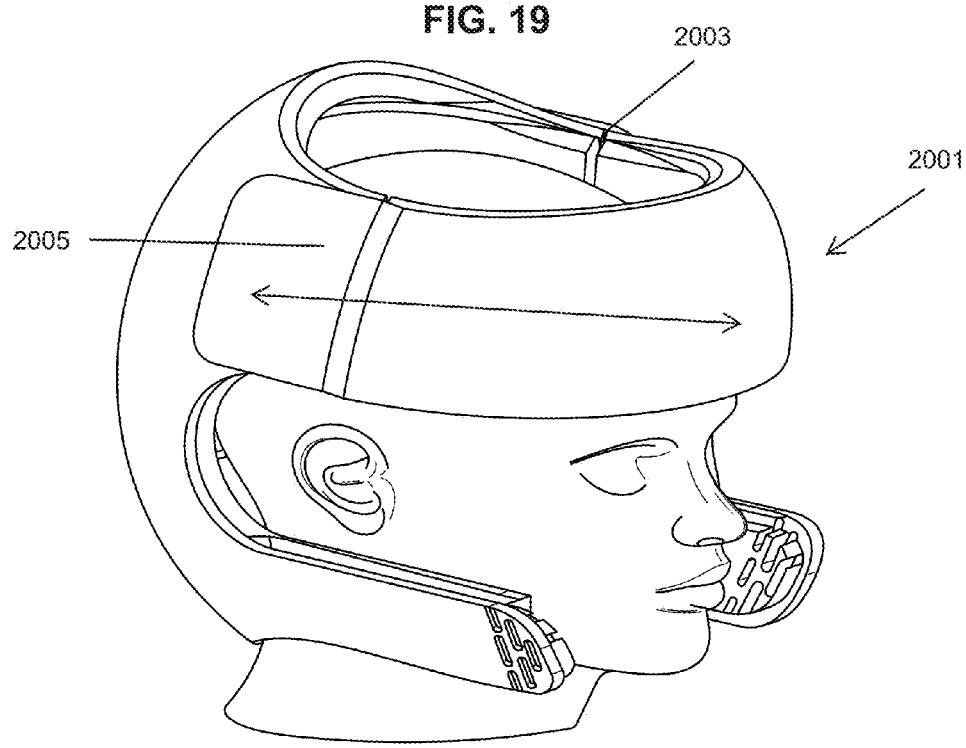
FIG. 20 is another embodiment of a helmet according wherein the top portion is expandable.

Referring now to FIG. 20, a helmet 2001 according to one embodiment of the present invention is illustrated. A front to back adjustment 2003 is shown which allows expansion in the direction of the arrows at the front top portion 2005 of the helmet relative to the back top portion of the helmet. The top portion expands to fit different head sizes. The lateral element extends from the back of the helmet and is integral thereto.

Figure 21:
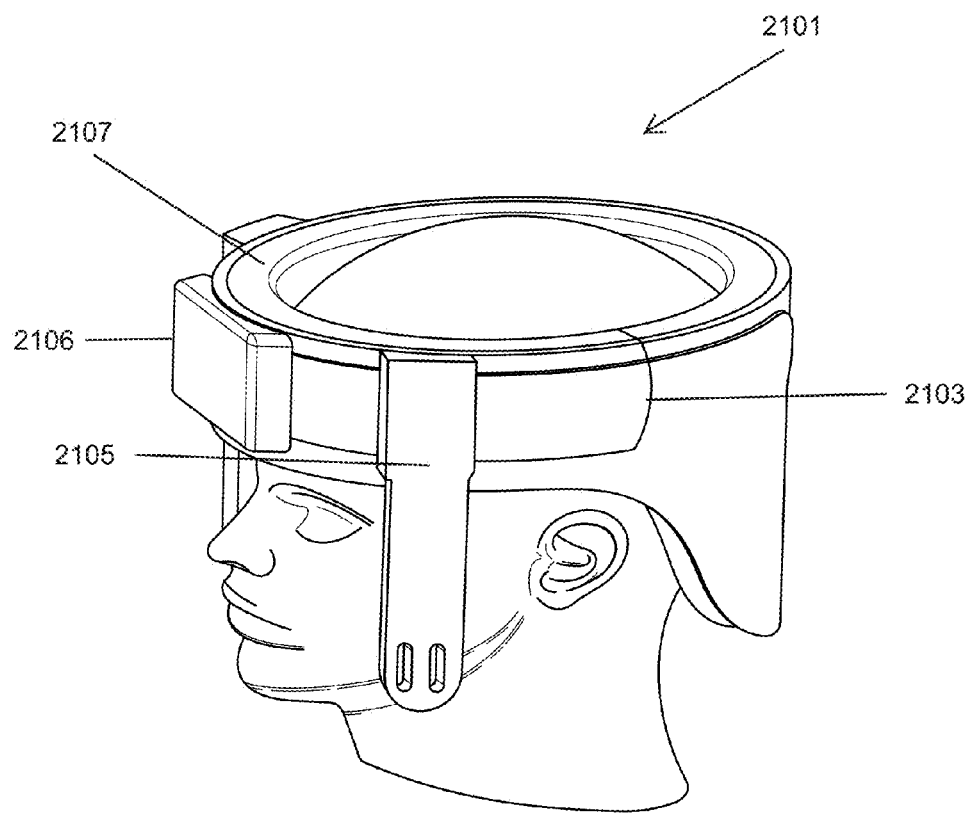
FIG. 21 is another embodiment of a helmet wherein the side lateral element extends from the top of the helmet.

Referring now to FIG. 21, a helmet 2101 is illustrated according to one embodiment of the present invention. Moveable mount 2105 adjusts front to back to position the lateral element closer to or more distant relative to the nose. A pad 2107 is positioned between the skull and the helmet frame. The circumference of the helmet is adjustable via adjustment 2103. Stabilizer 2106 is positioned at the front of the helmet. In one embodiment there is a moveable mount of the other side of the helmet also.

Figure 22:
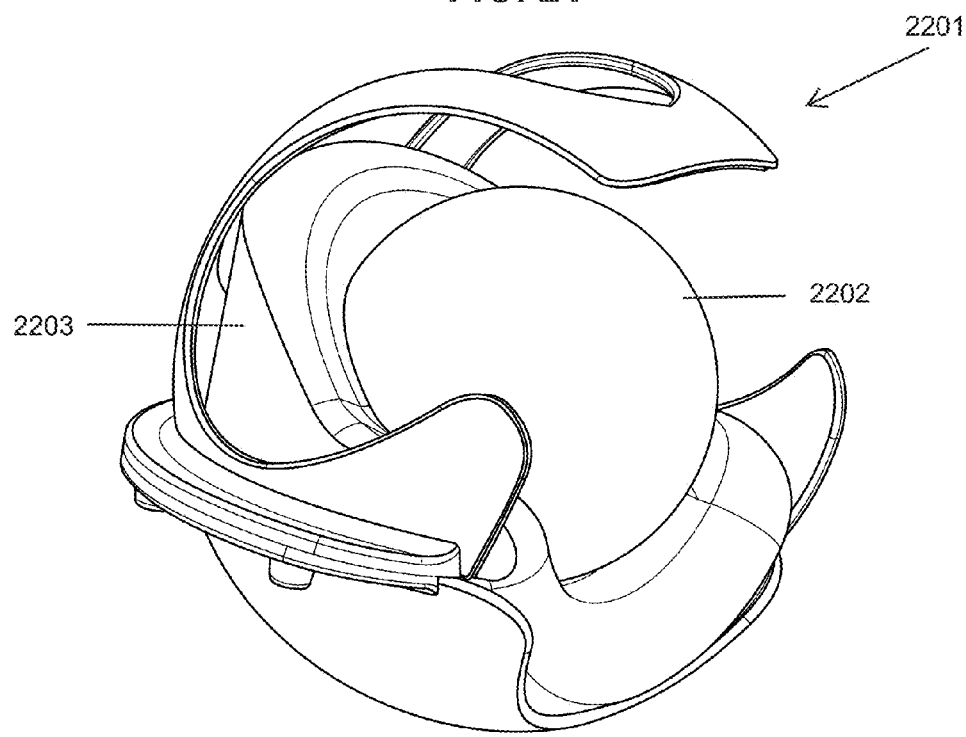
FIG. 22 is another embodiment of a helmet.

Referring now to FIG. 22, a helmet 2201 according to one embodiment of the present invention is illustrated. A molded pad 2203 separates the helmet from the skull 2202.

Figure 23:
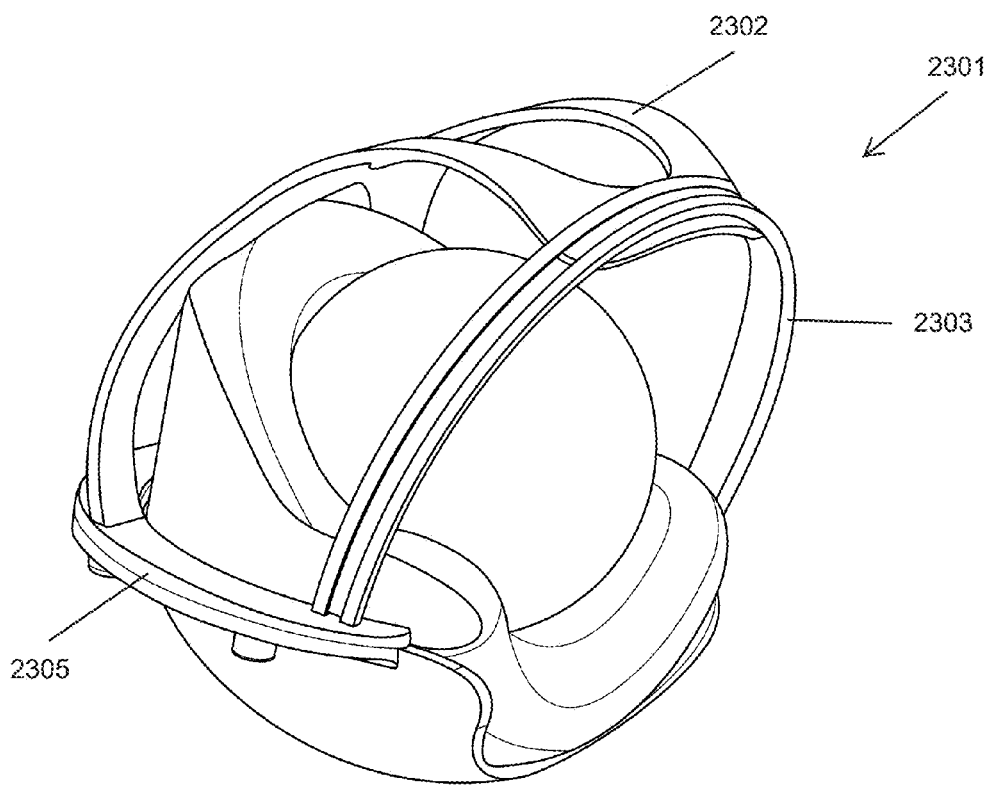
FIG. 23 is another embodiment of a helmet.

Referring now to FIG. 23, a helmet 2301 according to another embodiment of the present invention is illustrated. Mounting band 2303 attached to the lateral element 2305 and the top portion 2302 of the helmet.

Figure 24:
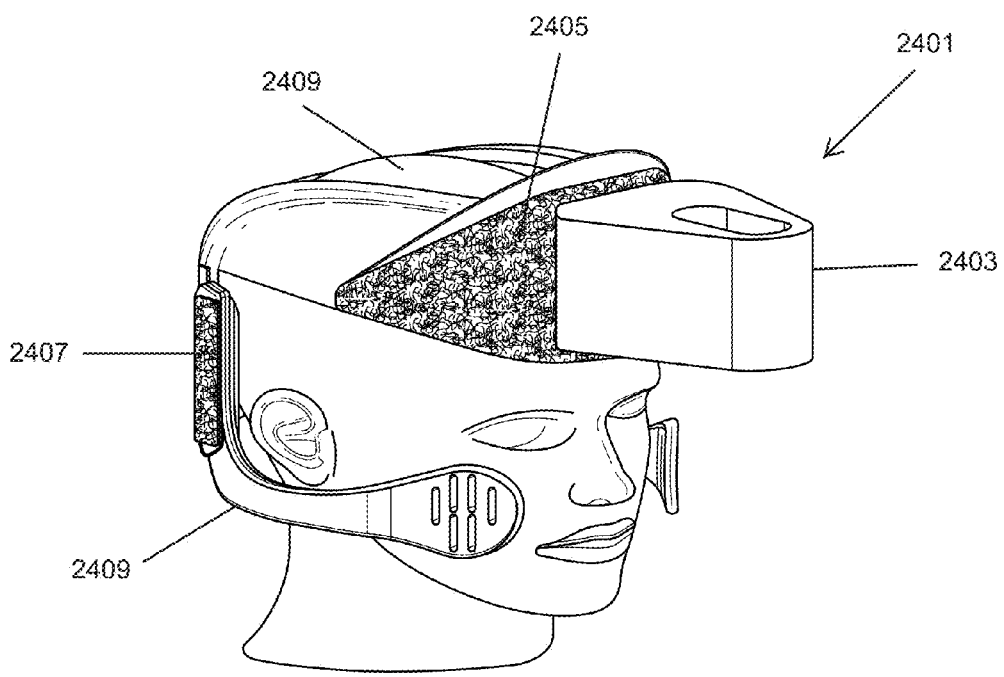
FIG. 24 is another embodiment of a helmet having a hub.

Referring now to FIG. 24, a helmet 2401 according to another embodiment of the present invention is illustrated. A hub 2403 is attached to the stabilizer 2405 at the top portion of the helmet. The stabilizer has a large area 2405 on the front of the helmet that may be covered in whole or in part with Velcro. An open area 2409 is in the top portion of the helmet. A lateral side element 2409 extends from the back portion of the helmet.

Figure 25:
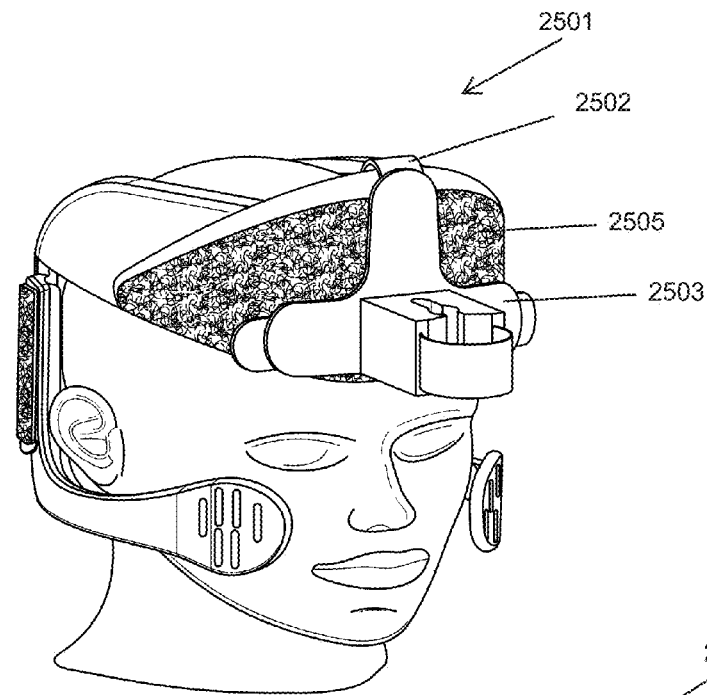
FIG. 25 is another embodiment of a helmet having a hub.

Referring now to FIG. 25, a helmet 2501 is illustrated according to one embodiment of the present invention. Hub 2503 is attached to stabilizer 2505. The hub could be foam or molded plastic and may be attached to the stabilizer via Velcro which is on the face of the stabilizer or with tabs. The hub 2503 is a t-shape with tabs that can fold over the edge of the front of the helmet to secure the hub in place. The hub contains an opening which securely holds the conduit in place once the conduit is positioned therein. The hub opening may be adjustable to accommodate different size conduits.

Figure 26:
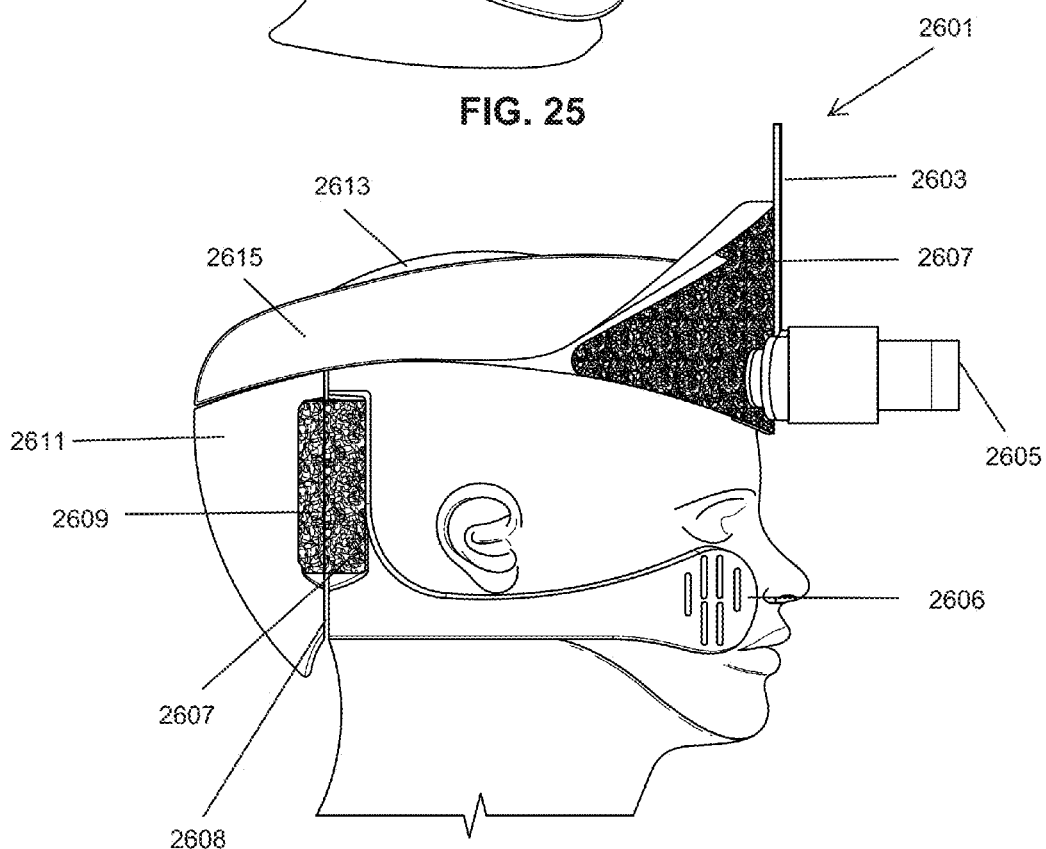
FIG. 26 is a side view of the helmet in FIG. 25.

Referring now to FIG. 26, a right side view of helmet 2501 is illustrated. A hinge 2609 permits flexibility of the lateral side element 2606 away from the face for positioning the helmet on the head. Additionally Velcro or other attachment means 2609 can be placed on the side of the element for positioning a strap that secures the patient airway interface and or eye or ear flaps against the face. The back portion 2611 of the helmet is separated from the lateral side element 2606 by a segment 2608. The front of the helmet is positioned lower on the forehead. Tab 2603 attached to hub 2605 is shown in the pre-affixed position. The front face of the helmet 2607 acts to stabilizer the hub.

Figure 27:
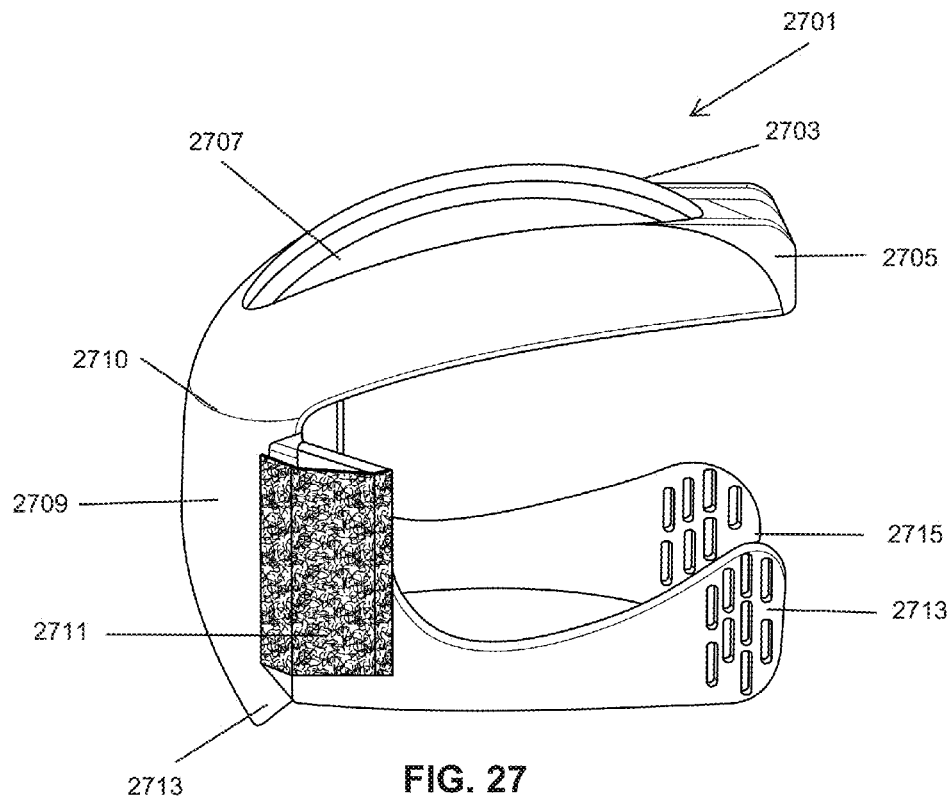
FIG. 27 is another embodiment of a helmet.

Referring now to FIG. 27, a helmet 2701 according to one embodiment of the present invention is illustrated. A top portion 2703 having an open area in the top 2707 is shown. A back portion 2709 is curved and is connected to the lateral side elements 2713 and 2715 via a hinge 2711. A seam 2710 segments the back portion from the top portion 2703. A stabilizer 2705 is shown in the front top portion of the helmet.

Figure 28:
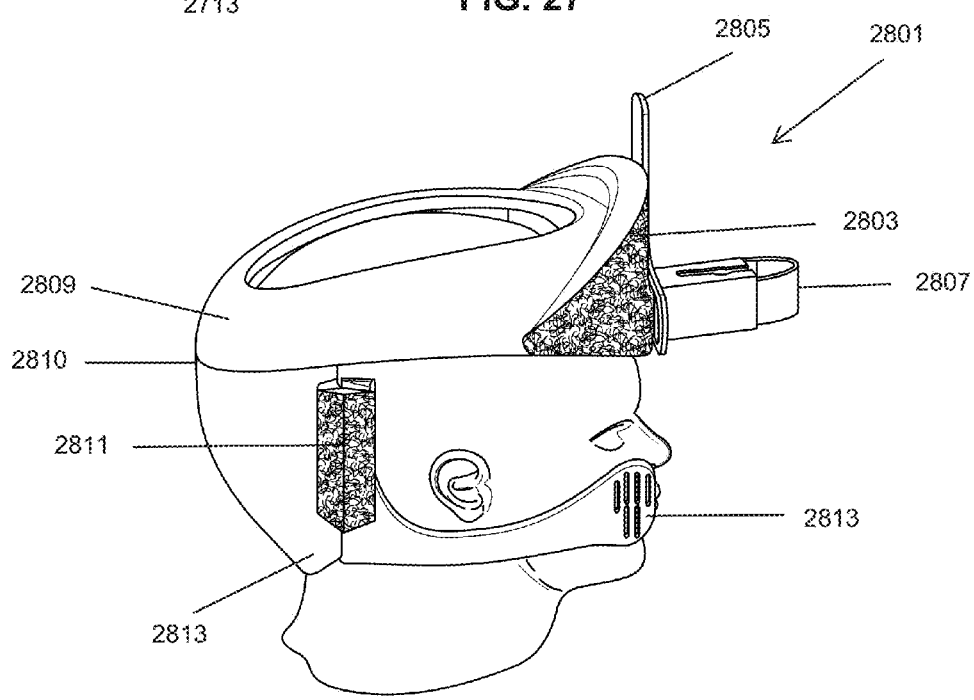
FIG. 28 is embodiment side perspective view of a helmet of FIG. 26.

Referring now to FIG. 28, a helmet 2801 is illustrated according to one embodiment of the present invention. A top portion 2809 having a seam 2810 and hub 2807 for conduit is attached to the front of the helmet. The front of the helmet may be covered with Velcro. The bottom portion of the helmet is curved 2813 and the lateral side element is hingedly connected 2811 to the back portion of the helmet.

Figure 29:
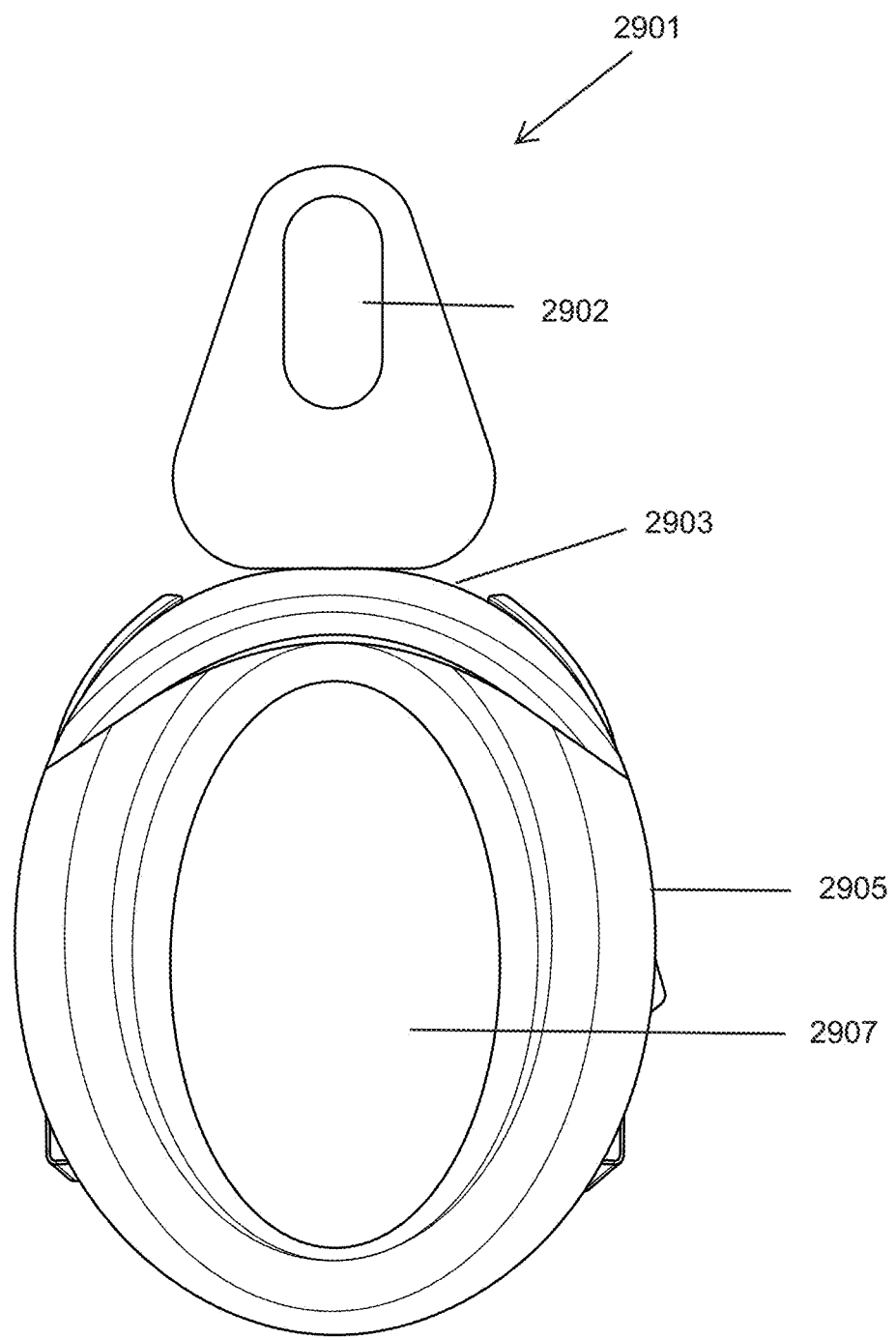
FIG. 29 is a top view of the helmet illustrated in FIG. 28.

Referring now to FIG. 29, a top view of the helmet of FIG. 28 is illustrated. A hub 2903 for conduit is seen having an open area 2902 through which the conduit passes. An open area in the top portion 2907 of the helmet allows access to the head in the area of the frontal bone. The hub is attached to the front face of the top portion of the helmet.

Figure 30:
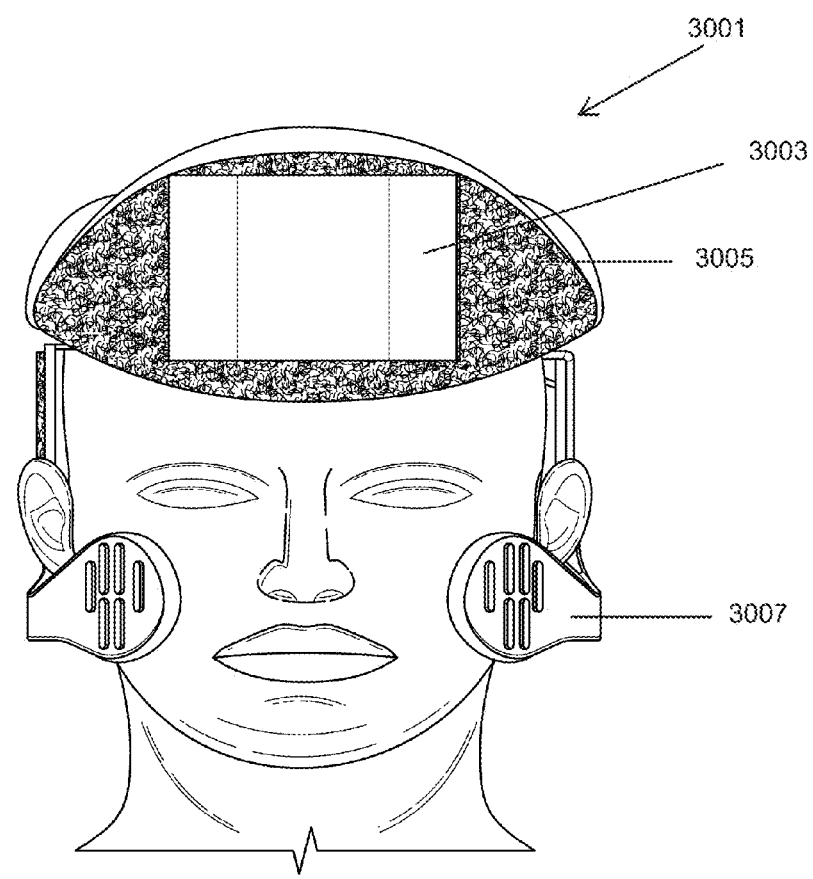
FIG. 30 is a front view of the helmet illustrated in FIG. 28.

Referring now to FIG. 30, a helmet 3001 according to another embodiment of the present invention is illustrated. A front on view of the hub 3003 is attached to the front portion of the helmet. Velcro covers all or a portion of the front portion of the helmet and attaches the hub to the helmet.

Figure 31:
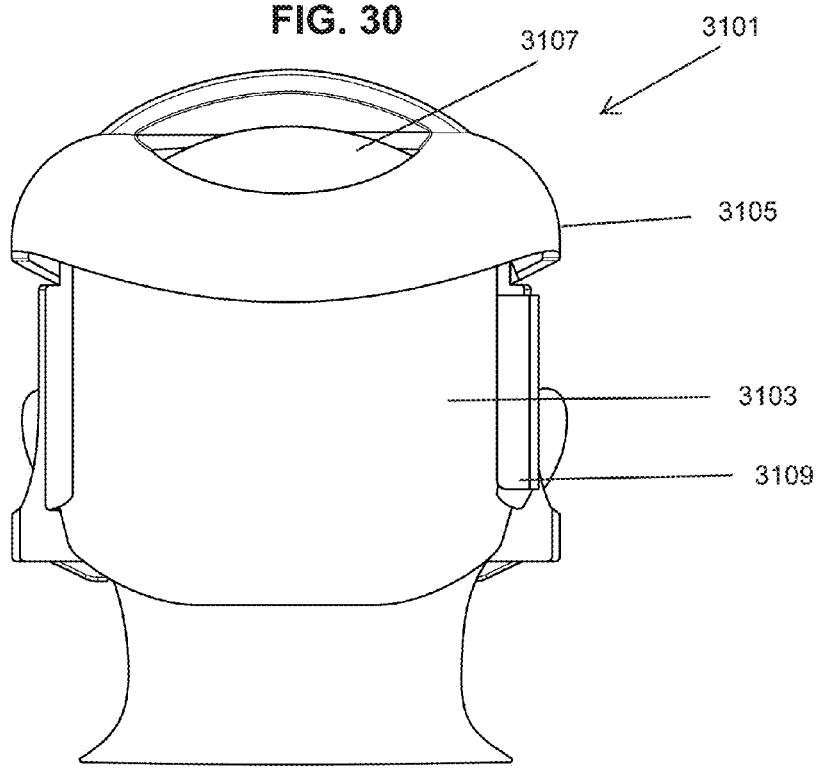
FIG. 31 is a back view of the helmet illustrated in FIG. 30.

Referring now to FIG. 31, a back portion of helmet 3001 is illustrated in 3101. An opening 3107 in the top portion 3105 of the helmet permits access to the skull. The back portion 3103 and hinge 3109 are also illustrated.

Figure 32:
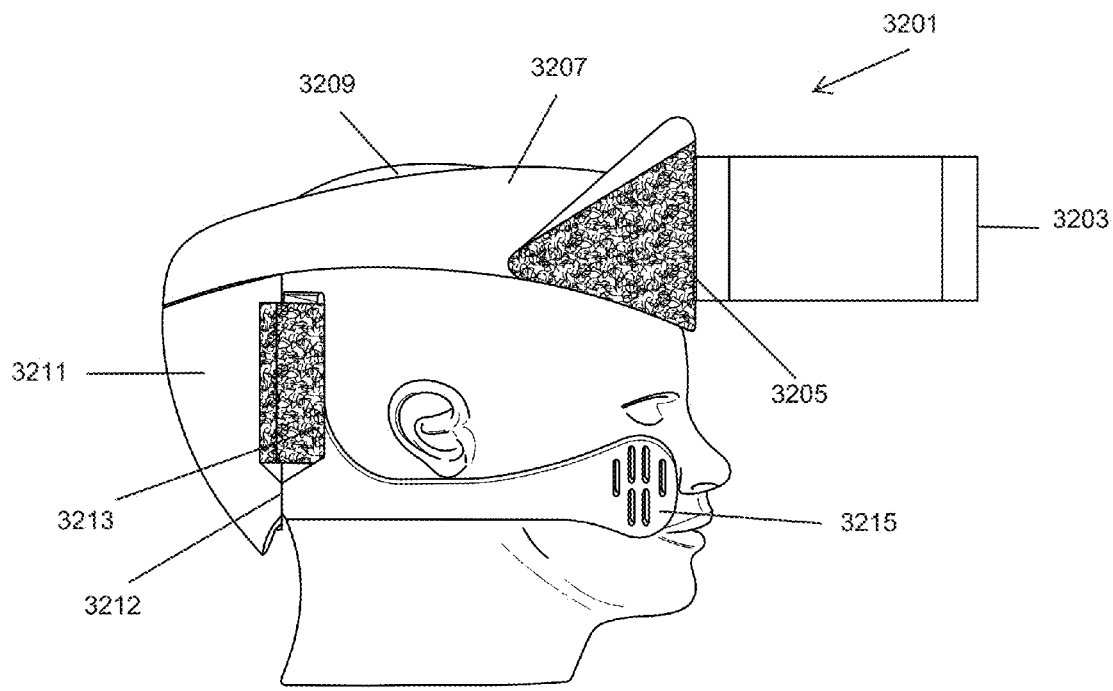
FIG. 32 is right side view of the helmet of FIG. 28.

Referring now to FIG. 32 a side view of helmet 3001 is illustrated with a hub 3203 associated with the front face 3205 of the top portion 3207 of the helmet. The top of the head is accessible through opening 3209 of the helmet. The back portion 3211 is separated from the right lateral side element 3215 by seam 3212.

Figure 33:
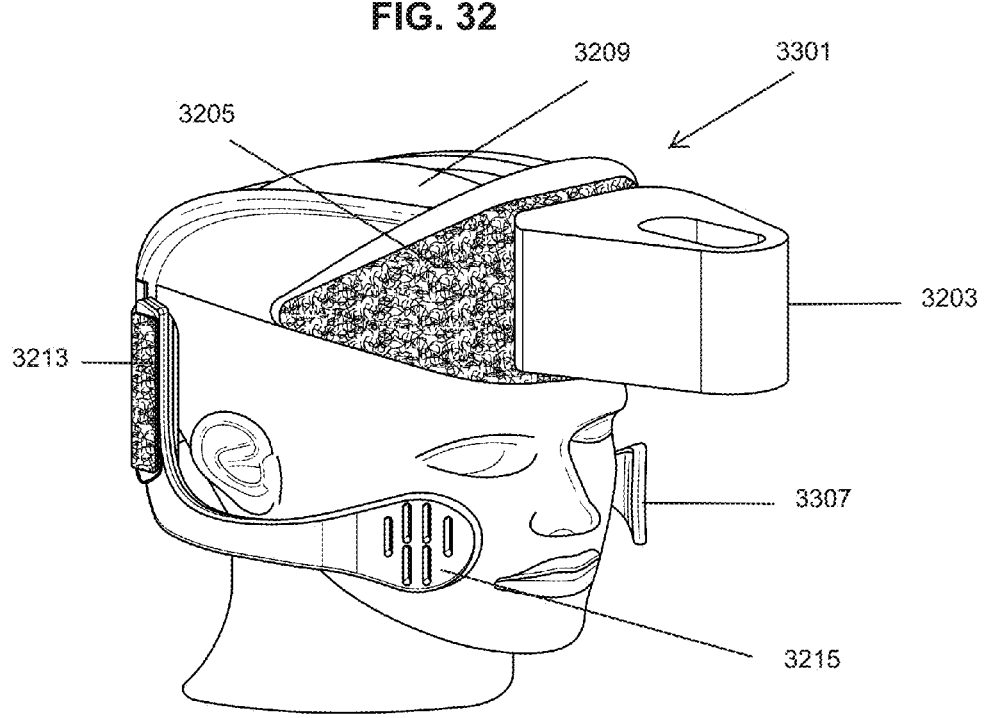
FIG. 33 is a perspective view of the helmet of FIG. 28.

Referring now to FIG. 33 a perspective view of helmet 3001 is illustrated with a hub 3203 attached to the front face 3205 of the helmet.

Figure 34:
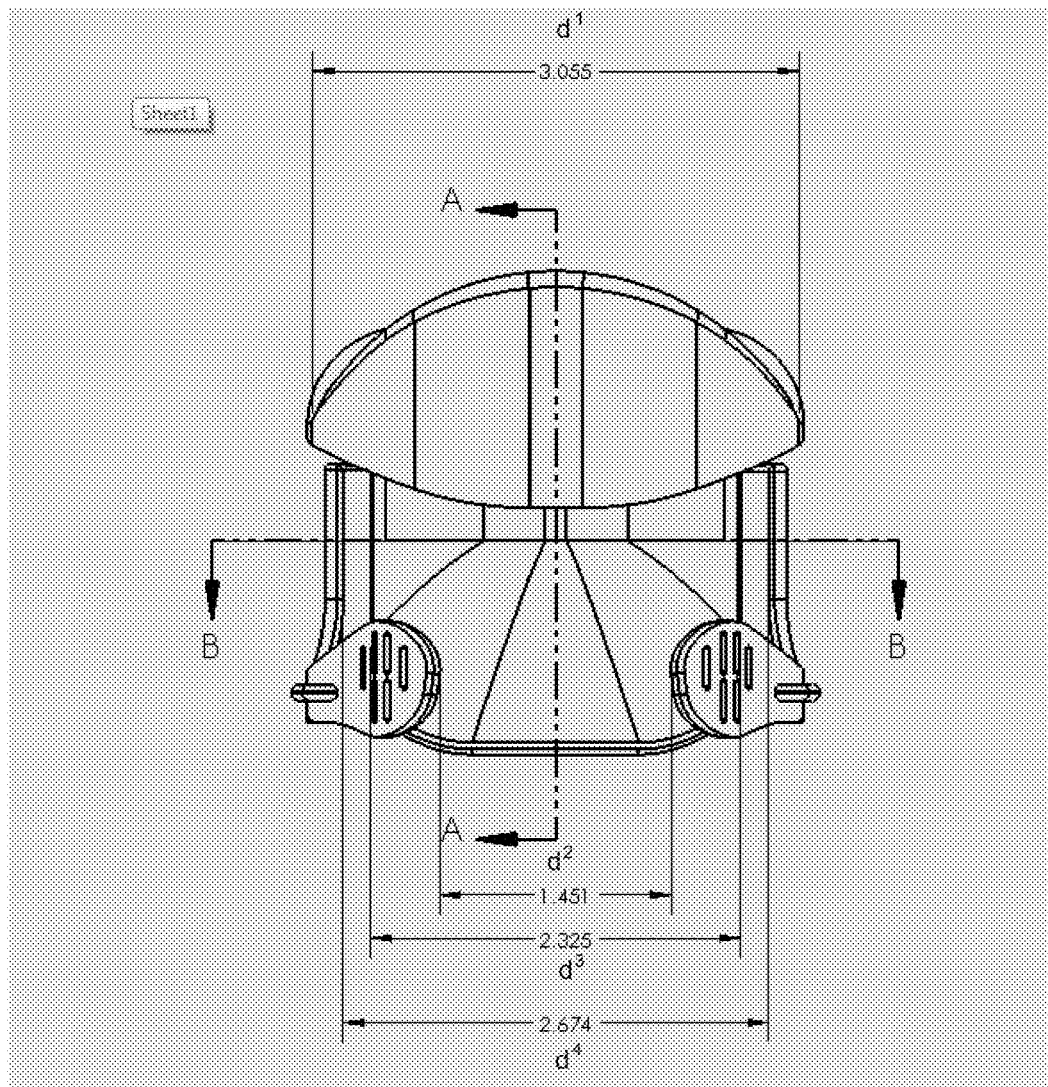
FIG. 34 is a diagram view of one embodiment of the present invention with measurements for a neonate.

Referring now to FIG. 34, a diagram of a helmet according to one embodiment of the present invention is presented with measurements for a neonate head. Distance $d^1$ is the distance from the outer edge of the top portion of the helmet as shown. Distance $d^2$ is the distance between the two points of the inner edge of the right lateral side element and the left lateral side element as shown. Distance $d^3$ is the distance between the side lateral elements at the front curve. Distance $d^4$ is the distance between each front edge of the back vertical section of the lateral side elements as shown.

Figure 35:
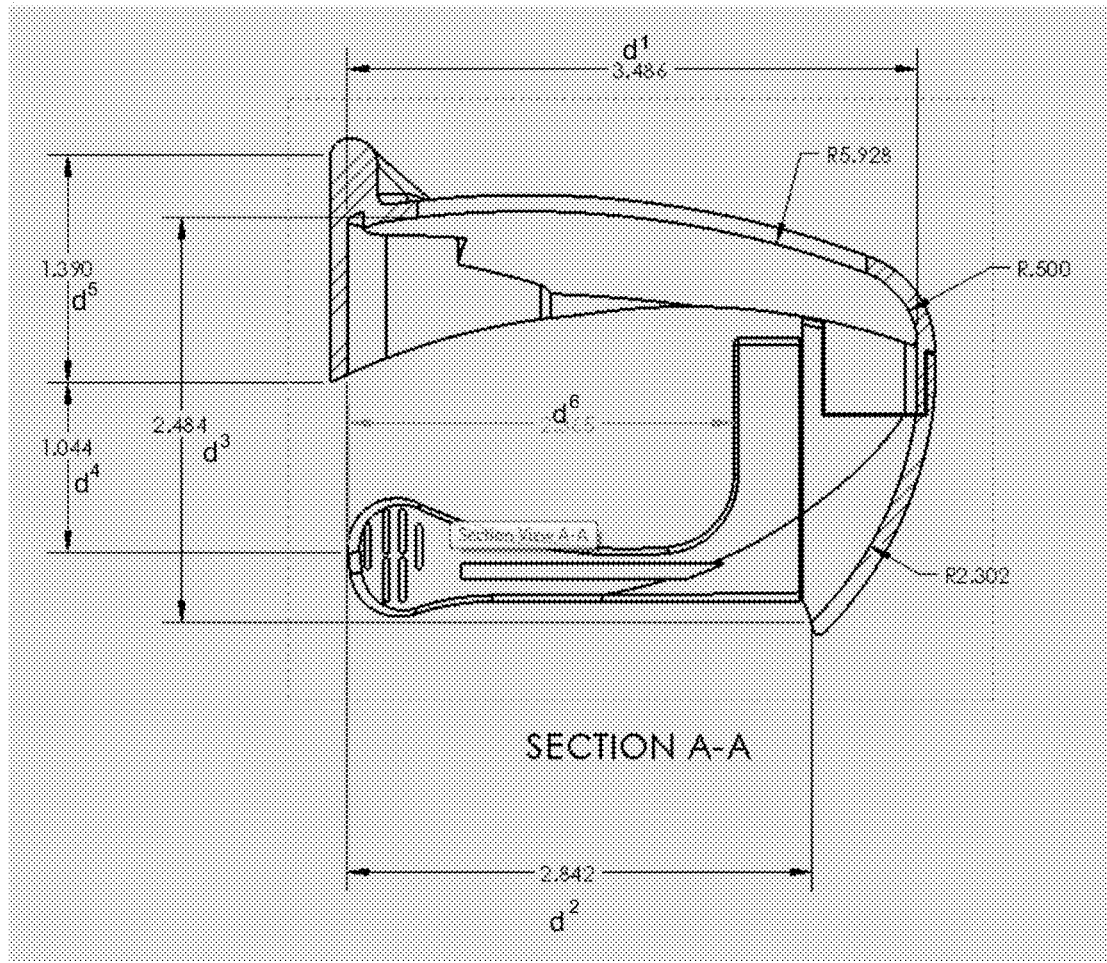
FIG. 35 is a section A-A view of FIG. 34 with measurements for a neonate.

Referring now to FIG. 35, a diagram of a helmet according to FIG. 34 (cut A-A) is presented with measurements for a neonate head. Distance $d^1$ is the distance between the internal curve of the top portion of the helmet and the curve at the back portion of the helmet as shown. Distance $d^2$ is the distance between the front edge of the lateral side element and the back portion of the helmet where it ends as shown. Distance $d^3$ is the distance between the front most point in the opening of the helmet and the back portion of the bottom of the helmet where it ends as shown. Distance $d^4$ is the distance between the front bottom edge of helmet and the middle of lateral side element as shown. Distance $d^5$ is the distance between the bottom face of front edge of helmet and the top face of front edge of Hemet as shown. Distance $d^6$ is the distance between the front edge of the lateral side element vertical member and the front face of the front edge of the lateral side element as shown. The curve of the helmet is indicated by the radius at several locations around the top and back of the helmet as shown.

Figure 36:
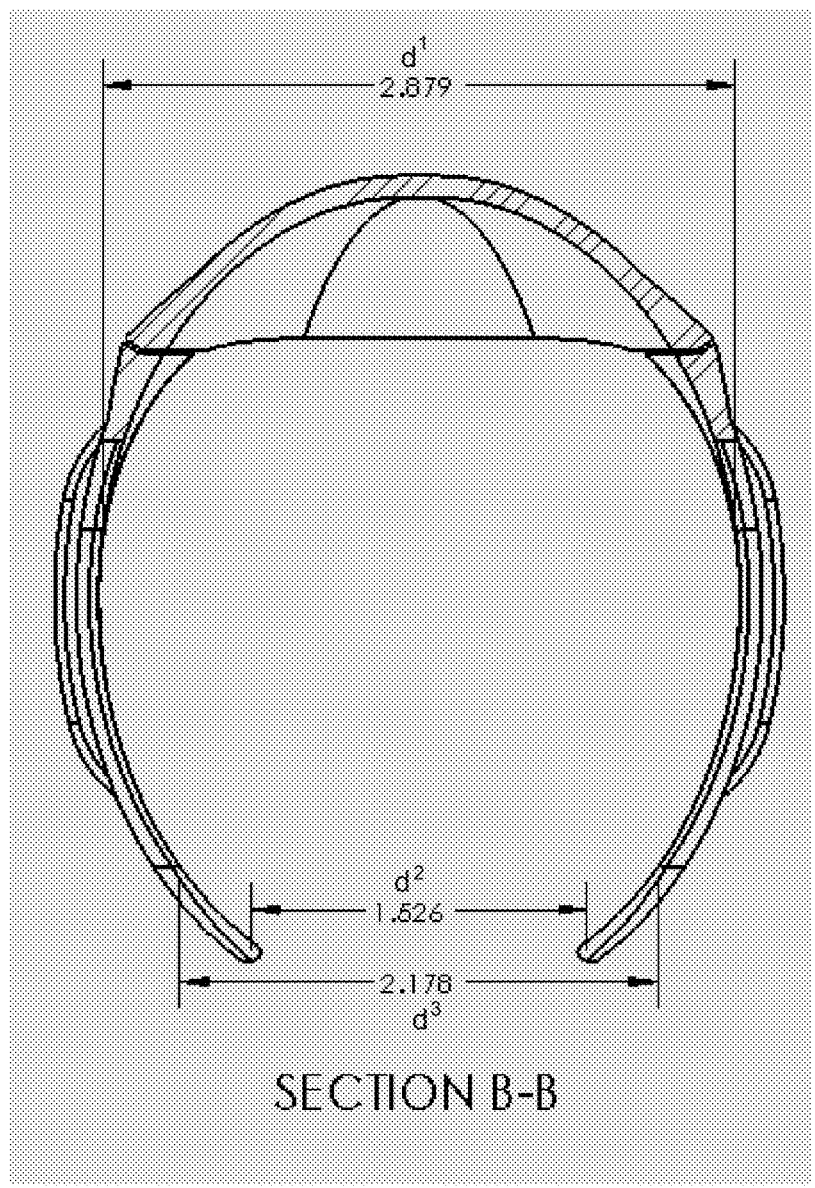
FIG. 36 is a section B-B view of FIG. 35 with measurements for a neonate.

Referring now to FIG. 36, a diagram of a helmet according to FIG. 34 (cut B-B) is presented with measurements for a neonate head. Distance $d^1$ is the distance between the back edge of each lateral side element. Distance $d^2$ is the distance between the end of the lateral side elements at the inner surface as shown. Distance $d^3$ is the distance between the lateral side element front portion inner surface as shown. The dimensions explained if FIG. 34-36 can be increased proportionally to increase larger head sizes and the measurements provided are represented as approximate and may vary (+/−20%).

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. For example, the helmets can be adjustable to accommodate various size skulls. The helmet can be manufactured of a plastic or composite made of acrylonitrile butadiene styrene, high density polyethylene, polyurethane, nylon, polycarbonate, polypropylene, or any combination thereof but not limited thereto. The entire disclosures of all references, applications, patents, and publications cited above are hereby incorporated by reference.

What is claimed is:

1. A headgear for securing a patient airway interface device to a patient's head comprising:
   a concave partial rigid helmet having an outer surface and an inner surface and having a left lateral element, a right lateral element, a top portion and a back portion, wherein the left lateral element and the right lateral element are separated at a front half of the concave partial helmet by a void between a front half top portion of the concave partial helmet and the left lateral element and the right lateral element, wherein the back portion of the concave partial rigid helmet is rigid and is structured to overlay the patient's skull when the headgear is in use:
   when on the patient's head the top portion of the concave partial helmet terminates at the forehead of the patient's head with a front face of the top portion of the concave partial helmet that is proximal to the forehead having a stabilizer for supporting a hub and wherein the left lateral element and the right lateral element are structured to terminate on either side of a patient's face overlaying a cheek portion without directly touching the cheek portion and wherein a section of the right lateral element and the left lateral element that is overlaying the cheek portion includes an opening that permits passage of a strap from the outer surface to the inner surface and wherein the back portion of the concave partial helmet that is structured to overlay the back half of the skull when the headgear is in use is separated from the patient's head by a pliable material that is attached to the inner surface of the concave partial helmet.

2. The headgear of claim 1 wherein the top portion of the concave partial helmet includes an open portion to allow access to a fontanel area of the patient's head.

3. The headgear of claim 1 wherein the left lateral element and the right lateral element of the concave partial helmet covers an ear and includes a removable noise abatement cover that when removed leaves an opening in the left lateral element or the right lateral element at a position over the ear.

4. The headgear of claim 1 wherein the back portion of the concave partial helmet is structured to overlay an occipital bone area of the patient's head.

5. The headgear of claim 1 wherein the left lateral element of the concave partial helmet and the right lateral element of the concave partial helmet are moveably connected with a connector to the back portion of the partial helmet.

6. The headgear of claim 5 wherein the connector is a hinge.

7. The headgear of claim 1 wherein a portion of the inner surface of the concave partial helmet that is structured to overlay a back portion of the skull when the headgear is in use is separated from the patient's head by a pliable material that is attached to the inner surface.

8. The headgear of claim 7 wherein the pliable material is connected to the inner surface releasably, the pliable material will remain in conformity with the natural shape of the head while in use.

9. The headgear of claim 7 wherein the pliable material is covered by a washable lining.

10. A gas delivery system adapted to provide a flow of gas to an airway of a patient, the system comprising:
    a headgear for securing a patient airway interface to a patient's head, the headgear comprising a concave partial helmet of claim 1; and
    a gas delivery conduit comprising the patient airway interface with an airway interface support having straps for securing the patient airway interface to the concave partial helmet at a position in relation with a patient's nostril for delivery of gas under pressures to the nostril.

11. The gas delivery system of claim 10 wherein the gas delivery conduit is attached to the concave partial helmet by a hub attached to a stabilizer on a front of the concave partial helmet, the hub having an opening through which passes the gas delivery conduit at an angle to the hub which allows the patient airway interface device positioned at a first end of the gas delivery conduit to be immediately adjacent to the nostril of a patient wearing the concave partial helmet.

12. The gas delivery system of claim 10 wherein the gas delivery conduit at a second end extends above the hub.

13. The gas delivery system of claim 10 wherein an eye patch may be tethered to the concave partial helmet when the patient is in need thereof.

14. The gas delivery system of claim 10 wherein the strap is secured to the concave partial helmet via an opening in a left lateral element of the concave partial helmet and a right lateral element of the concave partial helmet.

15. The gas delivery system of claim 14 wherein the opening is a plurality of openings at different locations on a right lateral element of the concave partial helmet and a left lateral element of the concave partial helmet used to select a best angle for securing the patient airway interface relative to a patient's nostril.

16. A method of securing a patient airway interface to a helmet of claim 1 when positioned on a patient's head comprising the steps of:
    attaching a conduit for carrying gas under pressure to the patient wearing the headgear of claim 1 wherein the conduit has a first end and a second end wherein the first end is a patient airway interface that provides gas under pressure to a nostril of a patient when the patient airway interface is adjacent to the nostril and the second end extends above a hub attached to a top portion of a concave partial helmet of claim 1 when positioned on the patient's head; and
    securing the patient airway interface adjacent to the nostril of a patient with a strap positioned around the concave partial helmet and attached to the patient airway interface at an angle to hold the patient airway interface in contact with the nostril to deliver gas under pressure to the nostril of the patient.

17. The method of claim 16 wherein the conduit at its second end attaches to a hose for carrying gas under pressure.

18. The method of claim 16 wherein a strap passes from the inner surface of the helmet to the outer surface of the helmet through an opening in a lateral element of the helmet wherein the strap rests on the outside of the helmet after passing through the opening.

19. The method of claim 16 wherein the patient airway interface is positionable up or down, side to side and toward or away relative to the nostrils.

* * * * *